(12) United States Patent
Ichihashi

(10) Patent No.: US 10,036,701 B2
(45) Date of Patent: Jul. 31, 2018

(54) SENSING SYSTEM AND SENSING METHOD

(71) Applicant: FUJIFILM Corporation, Tokyo (JP)

(72) Inventor: Mitsuyoshi Ichihashi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/401,181

(22) Filed: Jan. 9, 2017

(65) Prior Publication Data

US 2017/0115208 A1    Apr. 27, 2017

Related U.S. Application Data

(63) Continuation of application No. PCT/JP2015/069979, filed on Jul. 13, 2015.

(30) Foreign Application Priority Data

Jul. 15, 2014   (JP) ................................ 2014-144743

(51) Int. Cl.
*G01J 4/00* (2006.01)
*G01N 21/21* (2006.01)
(Continued)

(52) U.S. Cl.
CPC .............. *G01N 21/21* (2013.01); *G01N 21/23* (2013.01); *G02B 5/30* (2013.01); *G02B 27/28* (2013.01);
(Continued)

(58) Field of Classification Search
CPC ........ G01N 21/21; G01N 21/23; G01N 21/86; G01N 2021/216; G07D 7/1205;
(Continued)

(56) References Cited

U.S. PATENT DOCUMENTS

2002/0084406 A1 *   7/2002  Thawley .................. G07D 7/12
                                                      250/225
2007/0242353 A1    10/2007  Kamijo et al.

FOREIGN PATENT DOCUMENTS

DE    10 2005 030288 A1    1/2007
JP        2003-096850 A    4/2003
(Continued)

OTHER PUBLICATIONS

Extended European Search Report dated Jun. 30, 2017, issued by the European Patent Office in counterpart EP Application No. 15821718.2.
(Continued)

*Primary Examiner* — Jamil Ahmed
(74) *Attorney, Agent, or Firm* — Sughrue Mion, PLLC

(57) ABSTRACT

The invention provides a method of sensing a target object due to a change in light intensity detected when the target object passes to cross a light path of circularly polarized light, in a state where circularly polarized light selectively including any one sense of right circularly polarized light and left circularly polarized light is sensed, and a system including: an emission unit which emits circularly polarized light; a target object movement unit; and a detection unit which senses circularly polarized light, in this order, in which the detection unit is at a position where light emitted from the emission unit is incident, a light path of light where the light emitted from the emission unit is incident to the detection unit intersects with the target object movement unit, and the sense of circularly polarized light selectively emitted by the emission unit and the sense of circularly polarized light selectively sensed by the detection unit are the same as each other. It is possible to sense various target objects by using an optical sensor with excellent sensitivity (Continued)

and decreased erroneous sensing in an arbitrary environment, by using the method and the system of the invention.

22 Claims, 2 Drawing Sheets

(51) Int. Cl.
    *G02F 1/13*     (2006.01)
    *G02B 5/30*     (2006.01)
    *G02B 27/28*     (2006.01)
    *G02F 1/00*     (2006.01)
    *G07D 7/1205*     (2016.01)
    *G01N 21/23*     (2006.01)
    *G01N 21/86*     (2006.01)

(52) U.S. Cl.
    CPC .............. *G02F 1/0045* (2013.01); *G02F 1/13* (2013.01); *G07D 7/1205* (2017.05); *G01N 21/86* (2013.01); *G01N 2021/216* (2013.01)

(58) Field of Classification Search
    CPC . G07D 7/12; G07D 7/122; G02B 5/30; G02B 27/28; G02F 1/00; G02F 1/01; G02F 1/0045; G02F 1/13
    See application file for complete search history.

(56) References Cited

FOREIGN PATENT DOCUMENTS

| | | |
|---|---|---|
| JP | 2008-058270 A | 3/2008 |
| JP | 2008-217023 A | 9/2008 |
| JP | 2011-149935 A | 8/2011 |
| JP | 2013-036888 A | 2/2013 |
| JP | 2013-037269 A | 2/2013 |
| WO | 02/44985 A1 | 6/2002 |

OTHER PUBLICATIONS

International Search Report for PCT/JP2015/069979, dated Oct. 6, 2015. [PCT/ISA/210].
Written Opinion for PCT/JP2015/069979, dated Oct. 6, 2015. [PCT/ISA/237].
International Preliminary Report on Patentability and translation of Written Opinion, dated Jan. 26, 2017, from the International Bureau in counterpart International Application No. PCT/JP2015/069979.
Office Action dated Jan. 30, 2018, from Japanese Patent Office in counterpart Japanese Application No. 2016-534411.

* cited by examiner

FIG. 1A
FIG. 1B
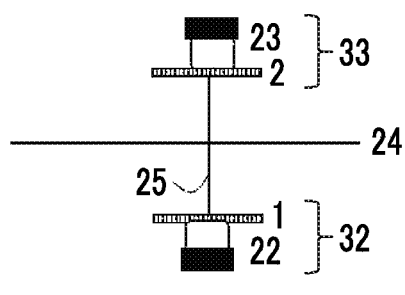
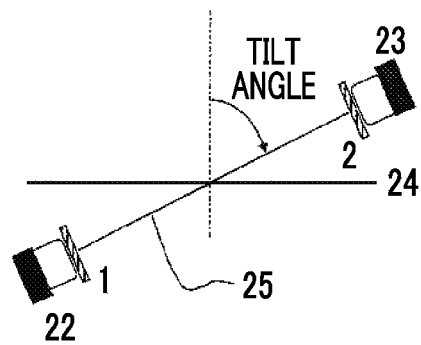
FIG. 1C
FIG. 1D
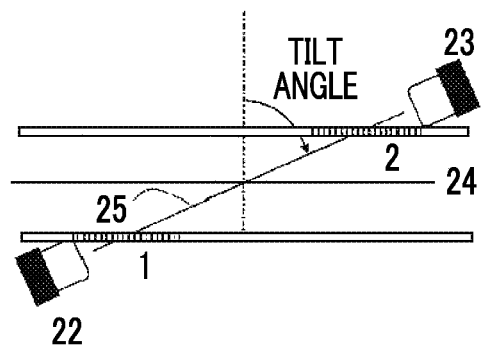
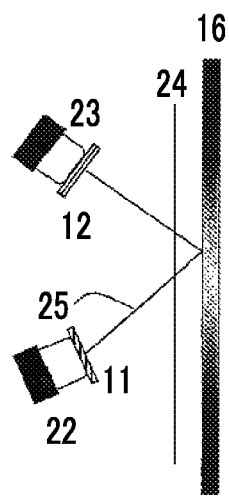

SENSING SYSTEM AND SENSING METHOD

CROSS-REFERENCE TO RELATED APPLICATIONS

This application is a continuation of PCT International Application No. PCT/JP2015/069979 filed on Jul. 13, 2015, which claims priority under 35 U.S. § 119(a) to Japanese Patent Application No. 2014-144743 filed on Jul. 15, 2014, the entire content of which is incorporated herein by reference.

BACKGROUND OF THE INVENTION

1. Field of the Invention

The present invention relates to a sensing system and a sensing method. More specifically, the invention relates to a sensing system and a sensing method utilizing circularly polarized light.

2. Description of the Related Art

Optical sensors are used in various fields and an optical sensor which detects a change in light intensity when a person enters an area in front of a door is used in an automatic door sensor. In addition, a banknote counter embedded in a vending machine or the like determines sizes of banknotes or reads printed patterns of banknotes by using an optical sensor.

A system using polarized light is known in the related art as a sensing system using an optical sensor. In JP2008-58270A, for example, cracks on a silicon substrate are detected with a system of irradiating the silicon substrate with polarized infrared light through a first linear polarizing filter and receiving reflected light or transmitted light from the silicon substrate through a second linear polarizing filter. The light intensity which can be sensed decreases, when the reflected light or transmitted light of a portion without cracks is linearly polarized light and travels through the second linear polarizing filter, except for a case where specific conditions are satisfied, however, this technology is acquired by using a phenomenon that light which can be sensed is generated even when the reflected light or transmitted light on the portion with cracks travels through the second linear polarizing filter due to diffuse reflection. In JP2013-36888A, a technology utilizing circularly polarized light in the technology of JP2008-58270A is disclosed. Here, a first circular polarizing filter which is provided in a light path of a beam between a light source and a silicon substrate, and a second circular polarizing filter which is on an extended line of the light path of a beam and is arranged on the silicon substrate a side opposite to a side where the first circular polarizing filter is arranged, have opposite polarization directions.

JP2003-96850A discloses an automatic faucet device which senses the hand of a person or an object using infrared light and prevents erroneous sensing using first polarizing means for allowing transmission of a linear polarized light component of floodlit infrared light and second polarizing means for allowing transmission of a linear polarized light component of infrared light emitted. In this device, light beams transmitted through the first polarizing means and the second polarizing means are different polarized light components, so as to detect diffuse reflection components and sense a target object.

SUMMARY OF THE INVENTION

In a system utilizing an optical sensor in the related art, erroneous sensing may be performed due to optical characteristics of a target object to be detected, and thus, the improvement regarding such a problem has been constantly desired. In JP2003-96850A, an example of a configuration in which erroneous sensing is decreased is disclosed and diffuse reflection in a case where a target object is in an environment where background light becomes mirror reflected light is sensed. In the technology disclosed in JP2008-58270A and the technology disclosed in JP2013-36888A utilizing circularly polarized light, diffuse reflection components from a target object in an environment where background light becomes mirror reflected light is detected in the same manner as described above.

An object of the invention is to provide a sensing system capable of being used in various environments or for a target object and having high sensitivity with decreased erroneous sensing. Another object of the invention is to provide a method of sensing various target objects by using an optical sensor with excellent sensitivity without erroneous sensing in an arbitrary environment.

In order to achieve the objects described above, the inventors have made intensive researches and found a new system. That is, the invention provides the following [1] to [20].

[1] A system which senses a target object including:
an emission unit which emits circularly polarized light;
a target object movement unit; and
a detection unit which senses circularly polarized light, in this order,
in which the detection unit is at a position where light emitted from the emission unit is incident,
a light path of light where the light emitted from the emission unit is incident to the detection unit intersects with the target object movement unit, and
the sense of circularly polarized light selectively emitted by the emission unit and the sense of circularly polarized light selectively sensed by the detection unit are the same as each other.

[2] The system according to [1],
in which the emission unit includes a light source and a circularly polarized light separation film 1,
the detection unit includes a circularly polarized light separation film 2 and a light receiving element,
the light source, the circularly polarized light separation film 1, the target object movement unit, the circularly polarized light separation film 2, and the light receiving element are disposed in this order, and
the circularly polarized light separation film 1 and the circularly polarized light separation film 2 allow selective transmission of circularly polarized light having the same sense.

[3] The system according to [2],
in which both of the circularly polarized light separation film 1 and the circularly polarized light separation film 2 are films including circularly polarized light separation layers obtained by fixing a cholesteric liquid-crystalline phase.

[4] A system which senses a target object including:
an emission unit which emits circularly polarized light;
a detection unit which senses circularly polarized light;
a target object movement unit; and
a mirror reflection member,
in which the target object movement unit is between the emission unit and the mirror reflection member and/or between the mirror reflection member and the detection unit,
the emission unit and the detection unit are at a position where the light emitted from the emission unit is mirror-reflected by the mirror reflection member and incident to the detection unit, a light path of the light which is emitted from the emission unit and incident to the mirror reflection member and/or a light path of the light which is sensed by the detection unit due to the reflection of the incident light by the mirror reflection member intersects with the target object movement unit, and the sense of circularly polarized light selectively emitted by the emission unit and the sense of circularly polarized light selectively sensed by the detection unit are opposite from each other.

[5] The system according to [4], in which the emission unit includes a light source and a circularly polarized light separation film 11, the detection unit includes a circularly polarized light separation film 12 and a light receiving element, the light source, the circularly polarized light separation film 11, and the mirror reflection member are included in this order, the mirror reflection member, the circularly polarized light separation film 12, and the light receiving element are included in this order, and the circularly polarized light separation film 11 and the circularly polarized light separation film 12 allow selective transmission of circularly polarized light having opposite senses.

[6] The system according to [4] or [5], in which both of the circularly polarized light separation film 11 and the circularly polarized light separation film 12 are films including circularly polarized light separation layers obtained by fixing a cholesteric liquid-crystalline phase.

[7] The system according to any one of [1] to [6], in which the target object is an object including a transparent part.

[8] The system according to any one of [1] to [6], in which the target object is an object including a transparent part and an opaque part.

[9] The system according to any one of [1] to [8], in which the target object has a sheet shape.

[10] The system according to [9], in which the target object is a banknote.

[11] The system according to [9] or [10], in which the target object movement unit is disposed so that the light path is tilted with respect to a normal direction of the plane of the target object, when the target object passes through the light path.

[12] The system according to [10], in which the target object is a banknote and the tilt direction is parallel with a short side direction of the banknote.

[13] A method of sensing a target object including:

sensing a target object due to a change in light intensity sensed when the target object passes to cross the light path of the circularly polarized light, in a state where circularly polarized light selectively including any one sense of right circularly polarized light and left circularly polarized light is sensed.

[14] The method according to [13], in which the change decreases.

[15] The method according to [13] or [14], in which the target object is an object including a transparent part.

[16] The method according to any one of [13] to [15], in which the target object is an object including a transparent part and an opaque part.

[17] The method according to any one of [13] to [16], in which the target object has a sheet shape.

[18] The method according to [17], in which the target object is a banknote.

[19] The method according to [17] or [18], in which the target object passes through the light path so that the light path is tilted with respect to a normal direction of the plane of the target object.

[20] The method according to [19], in which the target object is a banknote and the tilt direction is parallel with a short side direction of the banknote.

With the invention, a new system is provided as a sensing system utilizing an optical sensor. The invention also provides a new method as a method of sensing a target object with an optical sensor. It is possible to perform the sensing of various target objects including materials including transparent parts, for example, in an arbitrary environment with excellent sensitivity with decreased erroneous sensing by using the system or the method of the invention.

BRIEF DESCRIPTION OF THE DRAWINGS

FIGS. 1A to 1D are drawings showing arrangement examples of a light source, a light receiving element, and a circularly polarized light separation film for the sensing of a target object by using a system of the invention.

DESCRIPTION OF THE PREFERRED EMBODIMENTS

Figure 2A:
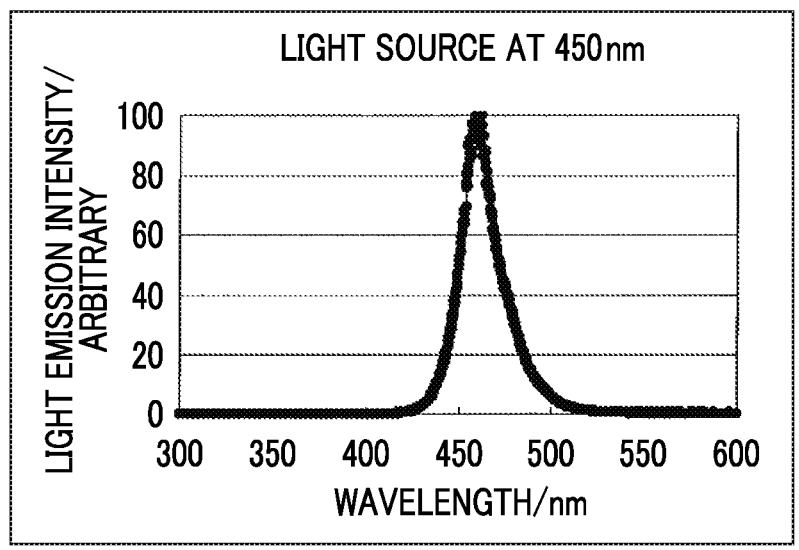
FIGS. 2A and 2B are drawings showing emission spectra of a light source used in examples.

Hereinafter, the invention will be described in detail.

A term "to" in this specification is used to include numerical values before and after the term as a lower limit value and an upper limit value.

In this specification, values of angles (for example, an angle such as "90°") and relationships thereof (for example, "parallel" and "horizontal") include acceptable ranges of error in the technical fields of the invention. For example, this means that an error is within a range of less than ±10° of an exact angle. An error of an exact angle is preferably equal to or smaller than 5° and more preferably equal to or smaller than 3°.

In this specification, a term "selectively" used when describing circularly polarized light means that the light intensity of any one of a right circularly polarized light component and a left circularly polarized light component of light is greater than the light intensity of the other circularly polarized light component. Specifically, when using the term "selectively", a degree of circular polarization of light is preferably equal to or greater than 0.3, more preferably equal to or greater than 0.6, and even more preferably equal to or greater than 0.8. The degree of circular polarization of light is substantially even more preferably 1.0. Here, when an intensity of the right circularly polarized light component of the light is set as $I_R$ and an intensity of the left circularly polarized light component is set as $I_L$, the degree of circular polarization is a value represented as $|I_R-I_L|/(I_R+I_L)$.

In this specification, a term "sense" used when describing circularly polarized light means the circularly polarized light is right circularly polarized light or left circularly polarized light. When the light is seen so that the light travels towards the front side, the sense of the circularly polarized light is defined as right circularly polarized light, in a case where a distal end of an electric field vector rotates clockwise according to passage of time, and is defined as left circularly polarized light, in a case where the distal end thereof rotates counterclockwise.

In this specification, the term "sense" may be used for a torsion direction of a spiral of a cholesteric liquid crystal. Regarding selective reflection by the cholesteric liquid crystal, right circularly polarized light is reflected and left circularly polarized light is transmitted, in a case where the torsion direction of the spiral of the cholesteric liquid crystal (sense) is right, and left circularly polarized light is reflected and right circularly polarized light is transmitted, in a case where the sense is left.

In this specification, a term "birefringence" means retardation of a target object at a wavelength (luminescence peak) of emitted light. When a target object is a film, a term "birefringence" includes in-plane retardation (Re) and retardation in a thickness direction (Rth) at a wavelength $\lambda$. The unit of both retardations is nm. Re at a specific wavelength of $\lambda$ nm is measured by emitting light at a wavelength of $\lambda$ nm in a film normal direction by using KOBRA 21ADH or WR (manufactured by Oji Scientific Instruments). The measurement can be performed by manually replacing a wavelength selection filter or converting a measured value by using a program or the like, when selecting a measurement wavelength of $\lambda$ nm. In a case where the film to be measured is expressed with a uniaxial or biaxial refractive index ellipsoid, Rth is calculated by using the following method.

Re at a specific wavelength of $\lambda$ nm on six points is measured by emitting light at a wavelength of $\lambda$ nm in a film normal direction using an in-plane slow axis (determined by using KOBRA 21ADH or WR) as a tilted axis (rotation axis) (in a case of no slow axis is present, an arbitrary direction in the film plane is set as a rotation axis), from a direction tilted from one side of the normal direction by 10 degrees to 50°, and Rth at a specific wavelength of $\lambda$ nm is calculated based on the measured retardation values, an assumed value of average refractive index, and an input film thickness value by using KOBRA 21ADH or WR. As described above, in a case of a film having a direction where a value of retardation at a certain tilt angle is zero, by using a slow axis in the plane from the normal direction is set as a rotation axis, a sign of a retardation value at a tilt angle greater than the tilt angle described above is changed to minus and the value is calculated by using KOBRA 21ADH or WR. The retardation values are measured from two arbitrarily tilted directions by using a slow axis as a tilted axis (rotation axis) (in a case of no slow axis is present, an arbitrary direction in the film plane is set as a rotation axis), and Rth can be calculated based on these values, an assumed value of average refractive index, and an input film thickness value by the following Expression (A) and Expression (B).

$$Re(\theta) = \left[ nx - \frac{ny \times nz}{\sqrt{\left(ny \sin\left(\sin^{-1}\left(\frac{\sin(-\theta)}{nx}\right)\right)\right)^2 + \left(nz \cos\left(\sin^{-1}\left(\frac{\sin(-\theta)}{nx}\right)\right)\right)^2}} \right] \times \frac{d}{\cos\left(\sin^{-1}\left(\frac{\sin(-\theta)}{nx}\right)\right)} \quad \text{Expression (A)}$$

Re ($\theta$) described above represents a retardation value in a direction tilted from the normal direction by an angle $\theta$. nx in Expression (A) represents a refractive index in a slow axis direction in the plane, ny represents a refractive index in a direction orthogonal to nx in the plane, and nz represents a refractive index in a direction orthogonal to nx and ny. d represents a film thickness.

$$Rth = ((nx+ny)/2 - nz) \times d \quad \text{Expression (B)}$$

[Light]

In this specification, light may be infrared light, visible light, ultraviolet light, or light in a wavelength range included in a wavelength range of infrared light and visible light, a wavelength range of visible light and ultraviolet light, or a wavelength range of infrared light, visible light, and ultraviolet light. The light may be light having a specific wavelength width of 1 nm, 10 nm, 50 nm, 100 nm, 150 nm, or 200 nm. The width is preferably equal to or greater than 50 nm. Two kinds of light rays, that is, two light rays in different wavelength ranges may be used.

Visible light is light having wavelengths which are visually recognizable by a person among electromagnetic waves and indicates light in a wavelength range of 380 nm to 780 nm. Infrared light (infrared light beam) is electromagnetic waves in a wavelength range which is longer than that of visible light and shorter than radiowaves. Near infrared light is electromagnetic waves in a wavelength range of 780 nm to 2500 nm. Ultraviolet light is electromagnetic waves in a wavelength range which is shorter than that of visible light and longer than that of X rays. The ultraviolet light may be light in a wavelength range that is distinguished from those of visible light and X rays, and is, for example, light in a range of a wavelength of 10 to 380 nm.

Near infrared light is also preferably used as light. In a case of using near infrared light as light, the wavelength range of near infrared light is preferably 780 nm to 1500 nm or 800 nm to 1500 nm. In general, light in a wavelength range corresponding to a wavelength range of near infrared light which is used in an infrared camera, an infrared photoelectric sensor, infrared communication, or the like may be used.

In this specification, a term "reflected light" has a meaning including mirror-reflected light (directly reflected light) and diffuse reflected light (scattered light). A term "transmitted light" has a meaning including scattered transmitted light, directly transmitted light, and diffracted light.

In this specification, a term "light path" means a path of light from a light source to a light receiving element. The light path is shown as a straight line in drawings or the like, but this does not mean that incident light and sensed light are limited to light having high directivity. The light path may simply show a shortest path of light.

[Polarized Light and Circularly Polarized Light]

In the sensing system and the sensing method of the invention, polarized light is used as light. By using polarized light, light from an irradiation unit can be dominantly sensed with respect to surrounding light and an S/N ratio can be increased. In addition, it is possible to sense a transparent target object. In the invention, circularly polarized light is used as polarized light for the sensing. When reflected light and transmitted light from a target object is sensed by using circularly polarized light, it is easy or unnecessary to adjust an azimuth of a film used for detection of polarized light, unlike in a case of using linearly polarized light as polarized light.

A polarized state of light can be measured using a spectral radiance meter or a spectrometer mounted on a circularly polarizing plate. In this ease, the intensity of light measured through a right circularly polarizing plate corresponds to $I_R$ and the intensity of light measured through a left circularly polarizing plate corresponds to $I_L$. The measurement can also be performed by attaching the circularly polarizing plate to an illuminometer or a spectrometer. A ratio can be measured by measuring the right circularly polarized light intensity by attaching a right circularly polarizing transmission plate and measuring the left circularly polarized light intensity by attaching a left circularly polarizing transmission plate.

[Target Object]

Any target object may be used as long as it has a function of blocking target object light to be sensed by a method using the system of the invention or the method of the invention. For example, the target object may have a light absorption function and a light reflection function. In the system and the method of the invention, circularly polarized light is used in the detection, and accordingly, a transparent part of an object including the transparent part can also be sensed. The transparent part may have birefringence. In this specification, the expression "having birefringence" means that Re or Rth is equal to or greater than 20 nm, in a case of a film or a plate-like product, for example, and Re or Rth is preferably equal to or greater than 50 nm, more preferably equal to or greater than 100 nm, and even more preferably equal to or greater than 200 nm. A polarization state of emitted circularly polarized light changes due to birefringence of a target object and this can cause a change occurrence of a change in light intensity detected by a detection unit.

In this specification, a term "transparency" means a state where natural light in a wavelength range of the light used in the sensing is transmitted. Specifically, light transmittance of a visible light region may be equal to or greater than 50%, equal to or greater than 60%, equal to or greater than 80%, equal to or greater than 90%, or equal to or greater than 95%. The light transmittance used as a scale of transparency can be calculated by using a method disclosed in JIS-K7105, that is, by measuring total light transmittance and scattered light quantity with an integrating sphere type light transmittance measuring device and subtracting diffuse transmittance from the total light transmittance.

Examples of a target object include a person, an animal, various industrial products, a card, paper, and a film. Specifically, examples of a target object including a transparent part include a PET bottle and various optical films. A target object including a transparent part and an opaque part is also preferable.

A banknote is also preferable as a target object. As a banknote, a banknote using a plastic material may be used. The banknote using a plastic material has advantages from viewpoints of hygiene, the lifetime of the banknote, and prevention of forged banknotes. In some countries, banknotes using a plastic material that are banknotes having a transparent part are used in order to prevent forged banknotes printed by a copying machine. The transparent part cannot be recognized or is difficult to be recognized in a banknote counter used in a cash dispenser or a vending machine. Accordingly, it is difficult to determine whether the banknote is present or the banknote is torn and this may cause malfunction. However, the system and the method of the invention can solve such a problem.

[Sensing Method and Sensing System]

In the method using the system of the invention or the method of the invention, in a state where circularly polarized light selectively including any one sense of right circularly polarized light and left circularly polarized light is sensed, a target object is sensed due to a change in light intensity sensed when the target object passes to cross the light path of the circularly polarized light. The change is preferably a change in which the light intensity decreases more than the light intensity when a target object is not present. When the light intensity decreases, the light intensity may be, for example, equal to or smaller than 80%, equal to or smaller than 50%, equal to or smaller than 20%, equal to or smaller than 10%, equal to or smaller than 5%, equal to or smaller than 1%, equal to or smaller than 0.5%, equal to or smaller than 0.1%, or equal to or smaller than 0.05% of the light intensity when a target object is not present.

The kind of a target object may be determined with an amount of change in light intensity. For example, a transparent product and an opaque product may be distinguished from each other.

The system of the invention may be a device at least including an emission unit which emits circularly polarized light, a target object movement unit, and a detection unit which senses circularly polarized light, or may have a combination including an emission unit which emits circularly polarized light and a detection unit which senses circularly polarized light and used for an arbitrary target object movement unit where a target object is moving (for example, inside of an elevator or a production line in a factory).

In one aspect (transmission type), the system includes an emission unit which emits circularly polarized light, a target object movement unit, and a detection unit which senses circularly polarized light, in this order. At this time, the detection unit is at a position where light emitted from the emission unit is incident, the light path of light where light emitted from the emission unit is incident to the detection unit intersects with the target object movement unit, and the sense of the circularly polarized light selectively emitted by the emission unit and the sense of the circularly polarized light selectively sensed by the detection unit are the same as each other.

In another aspect (reflective type), the system includes an emission unit which emits circularly polarized light, a detection unit which senses circularly polarized light, a target object movement unit, and a mirror reflection member. At this time, the target object movement unit is between the emission unit and the mirror reflection member and/or between the mirror reflection member and the detection unit, and the emission unit and the detection unit are at a position where the light emitted from the emission unit is mirror-reflected by the mirror reflection member and incident to the detection unit. A light path of the light which is emitted from the emission unit and incident to the mirror reflection member and/or a light path of the light which is directly sensed by the detection unit due to the reflection of the incident light by the mirror reflection member intersects with the target object movement unit, and the sense of the circularly polarized light selectively emitted by the emission unit and the sense of the circularly polarized light selectively sensed by the detection unit are opposite from each other.

FIG. 1 shows arrangement examples of a light source, a light receiving element, and a circularly polarized light separation film for sensing the target object.

In arrangements A, B, and C which are the aspect of the transmission type, a light source 22, a circularly polarized light separation film on a light source side (in this specification, may be referred to as a circularly polarized light separation film 1), a target object movement unit 24, a circularly polarized light separation film on a light receiving element side (in this specification, may be referred to as a circularly polarized light separation film 2), and a light receiving element 23 are arranged in this order. The circularly polarized light separation film 1 and the circularly polarized light separation film 2 transmit circularly polarized light having the same sense and light from the light source is directly sensed by the light receiving element, when a target object is not present. When light emitted from the emission unit passes through an intersection between a light path of light incident to the detection unit and the target object movement unit, light intensity of the light sensed by the light receiving element changes in accordance with optical characteristics of the target object and the target object is sensed due to the change. The target objects in the arrangements A, B, and C may move in a horizontal direction as a straight line shown in the drawings or may move back and forth of the space. In this specification, an expression "movement" of the target object may mean movement in one direction or reciprocating.

The arrangement D which is the aspect of the reflective type has a configuration in which reflected light is sensed by using the mirror reflection member 16, and a circularly polarized light separation film 11 transmits circularly polarized light having the sense opposite to that of a circularly polarized light separation film 12. In the arrangement D, the light source and the light receiving element are arranged on the same side surface side of the circularly polarized light separation film as seen from the target object. In this configuration, a layer which shields light may be provided between the light receiving element and the light source, so that the light receiving element is not affected by the direct light from the light source. The target object in the arrangement D may move in a vertical direction of the space as a straight line shown in the drawings or may move back and forth of the space.

In a case of sensing a sheet-shaped target object such as a banknote or a film including a transparent part, it is preferable that the light path forms an angle with a normal direction of the target object. That is, light is preferably obliquely incident to the target object. For example, in the arrangements B to F, a target object is preferably disposed to be parallel with the plane shown as the target object movement unit. This is because the birefringence of the plastic film having birefringence in the plane or in a thickness direction can reflect in the change in light intensity. The inventor have found in research, that, in the banknote having a transparent part (banknotes of the Canadian dollar, banknotes of Singapore, and banknotes of Vietnam), Re (550) which is in-plane retardation at a wavelength of 550 nm is approximately 0 to 100 nm and Rth (550) which is retardation in a thickness direction at a wavelength of 550 mu is approximately 500 to 1200 nm. It is preferable that such banknotes pass the intersection between the light path and the target object movement unit by setting a space horizontal direction of the target object movement unit shown in the arrangement B or the arrangement C of FIG. 1 to be parallel with a short side of the banknote. An angle formed by the light path and the normal direction of the target object (tilt angle shown in the arrangement B or the arrangement C of FIG. 1) may be 20° to 70°, greater than 20° and equal to or smaller than 70°, or 30 to 60°.

As shown in the arrangement D, a housing may be provided in the system of the invention so that the target object movement unit 24 shields light. At this time, as shown in the arrangement D, the circularly polarized light separation film may be provided on a window part of the housing.

Specific examples of the system include a banknote counter, a motion sensor used in an automatic door or an elevator, and a system which confirms the pass of a product in a production line in a factory. Examples of the product are not limited and a transparent product such as a film can also be sensed.

[Emission Unit]

The emission unit selectively emits circularly polarized light in a wavelength range of specific light. The wavelength range of the emitted light may be selected in accordance with a target object. The emission unit includes a light source. In addition, the emission unit preferably includes a light source, and a circularly polarized light separation film. In a case where the light source is a light source which emits linearly polarized light, the emission unit may include a light source and a phase difference film such as a λ/4 phase difference layer.

As the light source, any light source can be used as long as it emits light at a photosensitive wavelength of the light receiving element, such as a halogen lamp, a tungsten lamp, an LED, an LD, a xenon lamp, or a metal halide lamp, and an LED or an LD are preferable, from the viewpoints of a small size, emission directivity, monochromatic light, and pulse modification ability.

The emission unit preferably has, for example, a configuration in which the light source is included in a housing, the circularly polarized light separation film is arranged in a light emission portion, and the light other than light passing through the circularly polarized light separation film is not emitted from the light source. In a case where the circularly polarized light separation layer includes the linearly polarized light separation layer and the λ/4 phase difference layer, it is preferable that the λ/4 phase difference layer is disposed on the outer side and the linearly polarized light separation layer is disposed on the light source side.

[Detection Unit]

The detection unit may selectively sense circularly polarized light in a wavelength range of the light emitted from the emission unit.

The detection unit may be, for example, formed of a light receiving element and a circularly polarized light separation film.

Examples of the light receiving element include a photodiode type sensor using a semiconductor such as Si, Ge, HgCdTe, PtSi, InSb, or PbS, a detector in which light detecting elements are linearly arranged, or a CCD or a CMOS for acquiring an image.

The detection unit is preferably a light intensity detection unit capable of measuring light intensity.

As a component of the detection unit, the circularly polarized light separation film may be used by being bonding to the light receiving element which can detect light at wavelengths at which the circularly polarized light separation film selectively transmits any one of the right circularly polarized light and the left circularly polarized light. The circularly polarized light separation film may be disposed on the light receiving surface of the light receiving element.

The sensor preferably has a configuration in which the light receiving element is in a housing, the circularly polarized light separation film is arranged in a light receiving portion, and the light other than light passed through the circularly polarized light separation film does not approach the light receiving element. In a case where the circularly polarized light separation film includes a linearly polarized light separation layer which will be described later and a λ/4 phase difference layer, it is preferable that the λ/4 phase difference layer is disposed on the outer side and the linearly polarized light separation layer is disposed on the light receiving element side.

[Circularly Polarized Light Separation Film]

The circularly polarized light separation film is a film which selectively allows the transmission of any one of right circularly polarized light and left circularly polarized light in a specific wavelength range. It is preferable that the circularly polarized light separation film separates specific light (natural light or unpolarized light) which is incident from one side surface into right circularly polarized light and left circularly polarized light and selectively allows the transmission of any one thereof to the other side surface. At that time, the other circularly polarized light may be reflected or absorbed.

The circularly polarized light separation film may selectively allow the transmission of any one of right circularly polarized light and left circularly polarized light with respect to the light incident from any surface, or may selectively allow the transmission of any one of right circularly polarized light and left circularly polarized light with respect to only the light incident from one surface and may not allow the same selective transmission with respect to the light incident from the other side surface. When using the latter case, the arrangement for acquiring desirable circularly polarized light selectivity may be used. In addition, the circularly polarized light separation film may separate light incident from any surface into right circularly polarized light and left circularly polarized light and selectively allow the transmission of any one thereof to the other side surface, or may separate only the light incident from any one surface into right circularly polarized light and left circularly polarized light, selectively allow the transmission of any one thereof to the other side surface, and may not allow the circularly polarized light separation with respect to the light incident from the other side surface. When using the latter case, the arrangement for acquiring desirable circularly polarized light selectivity may be used.

Regarding the circularly polarized light separation film, light transmittance {(light intensity of transmitted circularly polarized light)/(light intensity of incident circularly polarized light)×100} of the circularly polarized light having the same sense as the incidence ray when any one of the right circularly polarized light and left circularly polarized light in a specific wavelength range having a width equal to or greater than 50 nm is incident, may be 70% or more, 80% or more, 90% or more, 95% or more, 99% or more, or substantially preferably 100%. At that time, light transmittance {(light intensity of transmitted circularly polarized light)/(light intensity of incident circularly polarized light)×100} of the circularly polarized light having the same sense as the incidence ray when the circularly polarized light having the other sense is incident in the same wavelength range described above, may be 30% or less, 20% or less, 10% or less, 5% or less, 1% or less, or substantially preferably 0%.

<Circularly Polarized Light Separation Layer>

The circularly polarized light separation film includes a circularly polarized light separation layer which selectively allows the transmission of any one of right circularly polarized light and left circularly polarized light in a specific wavelength range. In addition, in this specification, the circularly polarized light separation layer used on the light source side may be referred to as a circularly polarized light separation layer 1 and the circularly polarized light separation layer used on the light receiving element side may be referred to as a circularly polarized light separation layer 2. The circularly polarized light separation film includes the circularly polarized light separation layer so that the function of the circularly polarized light separation layer of selectively allowing the transmission of any one of right circularly polarized light and left circularly polarized light is not lost due to other layers, and accordingly, the circularly polarized light separation film has a function of selectively allowing the transmission of any one of right circularly polarized light and left circularly polarized light at least in a specific wavelength range.

A wavelength bandwidth of the wavelength range in which the circularly polarized light separation layer selectively allows the transmission of any one of right circularly polarized light and left circularly polarized light may be equal to or greater than 5 nm, equal to or greater than 10 nm, equal to or greater than 20 nm, equal to or greater than 30 nm, equal to or greater than 40 nm, or equal to or greater than 50 nm. The specific wavelength range in which the circularly polarized light separation layer selectively allows the transmission of any one of right circularly polarized light and left circularly polarized light may include wavelengths of light necessary for the detection of the target object in accordance with the usage state of the circularly polarized light separation film, and may be 50% or more, 60% or more, 70% or more, 80% or more, or 90% or more of the wavelength range of 800 nm to 1500 nm, and substantially 100% thereof.

The circularly polarized light separation layer may selectively allow the transmission, reflection, or absorption of light outside of the wavelength range in which any one of the right circularly polarized light and the left circularly polarized light is selectively transmitted. In addition, the circularly polarized light separation layer may selectively allow the transmission of any one of right circularly polarized light and left circularly polarized light, and may reflect or absorb the other circularly polarized light.

As the circularly polarized light separation layer, a layer obtained by fixing a cholesteric liquid-crystalline phase or a layer formed of a laminate including a linearly polarized light separation layer and a λ/4 phase difference layer can be used, for example.

(Reflected Light Scattering Circularly Polarized Light Separation Layer and Reflected Light Non-Scattering Circularly Polarized Light Separation Layer)

The circularly polarized light separation layer may include a reflected light scattering circularly polarized light separation layer. The reflected light scattering circularly polarized light separation layer has greater diffuse reflectance/specular reflectance of circularly polarized light having another sense, than scattering transmittance/straight transmittance of the circularly polarized light selectively transmitting at a specific wavelength. In this specification, the circularly polarized light separation film including the reflected light scattering circularly polarized light separation layer may be referred to as a scattering type circularly polarized light separation film and the circularly polarized light separation film not including the reflected light scattering circularly polarized light separation layer may be referred to as a mirror type circularly polarized light separation film.

The values of scattering transmittance/straight transmittance and diffuse reflectance/specular reflectance are respectively values calculated based on values measured by using a spectrophotometer and an integrating sphere unit. The straight transmittance and specular reflectance can be measured with a spectrophotometer and total angle measurement values of transmittance and reflectance can be measured by incorporating an integrating sphere unit into a spectrophotometer. The straight transmittance is a measurement value at an incidence angle of 0° and the specular reflectance may be, for example, a measurement value at an incidence angle of 5° for convenience of the measurement. The scattering transmittance can be calculated by subtracting the straight transmittance from the total angle measurement values of transmittance and the diffuse reflectance can be calculated by subtracting the specular reflectance from the total angle measurement values of reflectance. A filter which functions as a circularly polarized light filter at a measurement wavelength may be installed on the light source side, in order to measure straight transmittance, specular reflectance, and total angle measurement values of transmittance and reflectance of any one circularly polarized light.

The reflected light scattering circularly polarized light separation layer may be formed of a layer obtained by fixing a cholesteric liquid-crystalline phase, and the specific wavelength described above is a center wavelength of the circularly polarized light reflection (selective reflection) of a layer obtained by fixing a cholesteric liquid-crystalline phase which will be described later. The reflected light scattering circularly polarized light separation layer has great scattering properties of reflected light and transmitted light with respect to the circularly polarized light at a specific wavelength (selective reflection wavelength) of one sense. Meanwhile, reflected light scattering circularly polarized light separation layer has low scattering properties with respect to the circularly polarized light having the opposite sense. That is, in a case where the reflected light scattering circularly polarized light separation layer is formed of right helical cholesteric liquid crystal, for example, scattering properties of reflected circularly polarized light and transmitted circularly polarized light with respect to right circularly polarized light at the selective reflection wavelength are great and on the other hand, the scattering properties thereof with respect to left circularly polarized light may be low. In a case where the reflected light scattering circularly polarized light separation layer is formed of left helical cholesteric liquid crystal, for example, scattering properties of reflected circularly polarized light and transmitted circularly polarized light with respect to left circularly polarized light at the selective reflection wavelength are great and the scattering properties thereof with respect to right circularly polarized light may be low.

Regarding the reflected light scattering circularly polarized light separation layer, a value of scattering transmittance/straight transmittance of circularly polarized light having the sense described above at the specific wavelength is 0.00 to 0.10 and may be preferably 0.00 to 0.05. With such values, it is possible to ensure high light intensity and degree of circular polarization in a specific light path. In addition, regarding the circularly polarized light separation layer, a value of diffuse reflectance/specular reflectance of circularly polarized light having the opposite sense is 2.0 to 7.5 and may be preferably 3.0 to 5.0. When the value of diffuse reflectance/specular reflectance is greater than 7.5, the transparency of the circularly polarized light separation layer may decrease.

In addition, regarding the reflected light scattering circularly polarized light separation layer, a haze value measured with natural light at the specific wavelength described above is greater than 10 and equal to or smaller than 55 and may be preferably greater than 20 and equal to or smaller than 50. Here, the haze value is calculated as a value of {(scattering transmittance of natural light)/(scattering transmittance of natural light+straight transmittance of natural light)× 100(%)}. The haze value can be calculated based on values measured by using a spectrophotometer and an integrating sphere unit as described above for the measurement of scattering transmittance/straight transmittance of circularly polarized light, and at the time of the measurement, the measurement may be performed without using the filter which functions as the circularly polarized light filter on the light source side.

The circularly polarized light separation layer may be formed of only a reflected light non-scattering circularly polarized light separation layer which does not have reflected light scattering properties described above, may be formed of only the reflected light scattering circularly polarized light separation layer, or may be formed of the reflected light scattering circularly polarized light separation layer and the reflected light non-scattering circularly polarized light separation layer. In a case of a circularly polarized light separation layer formed of the reflected light scattering circularly polarized light separation layer and the reflected light non-scattering circularly polarized light separation layer, it is preferable that the reflected light scattering circularly polarized light separation layer is included on the outermost surface.

Regarding the reflected light non-scattering circularly polarized light separation layer, the scattering properties of reflected light and transmitted light with respect to the circularly polarized light at a specific wavelength (selective reflection wavelength) of one sense are substantially the same as the scattering properties with respect to the circularly polarized light having the opposite sense, a value of scattering transmittance/straight transmittance of circularly polarized light having the sense at the specific wavelength is 0.00 to 0.05 and preferably 0.00 to 0.03, and a value of diffuse reflectance/specular reflectance of circularly polarized light having the other sense is 0.00 to 0.05 and may be preferably 0.00 to 0.03. A haze value measured with natural light at the specific wavelength is equal to or smaller than 3.0 and may be preferably equal to or smaller than 1.0.

As the reflected light scattering circularly polarized light separation layer, a layer obtained by fixing a cholesteric liquid-crystalline phase may be used. As the reflected light non-scattering circularly polarized light separation layer, a layer obtained by fixing a cholesteric liquid-crystalline phase or a laminate including a linearly polarized light separation layer and a λ/4 phase difference layer may be used.

(Layer Obtained by Fixing Cholesteric Liquid-Crystalline Phase)

It is known that a cholesteric liquid-crystalline phase exhibits circularly polarized light selective reflection of selectively reflecting circularly polarized light having any one sense of right circularly polarized light and left circularly polarized light and transmitting circularly polarized light having the other sense. A number of cholesteric liquid-crystalline compounds or films formed from a cholesteric liquid-crystalline compound showing circularly polarized light selective reflection are known in the related art, and when using a layer obtained by fixing the cholesteric liquid-crystalline phase in the circularly polarized light separation film, the technologies of the related, art can be referred to.

The layer obtained by fixing the cholesteric liquid-crystalline phase may be a layer in which orientation of liquid crystal compounds to be the cholesteric liquid-crystalline phases is maintained, and typically, a layer obtained by setting a polymerizable liquid crystal compound to have an orientation state of a cholesteric liquid-crystalline phase, polymerizing and curing the compound by ultraviolet light irradiation and heating to form a layer having no fluidity, and at the same time, changing the state of the compound to a state where the orientation state is not changed by an external field or an external force. In addition, in the layer obtained by fixing the cholesteric liquid-crystalline phase, it is sufficient as long as optical properties of the cholesteric liquid-crystalline phase are maintained in the layer, and the liquid crystal compound in the layer may not show liquid crystalline properties. For example, the polymerizable liquid crystal compound may be polymerized by a curing reaction and lose liquid crystalline properties.

In this specification, the layer obtained by fixing the cholesteric liquid-crystalline phase may be referred to as a cholesteric liquid-crystalline layer or a liquid crystal layer.

The cholesteric liquid-crystalline layer exhibits circularly polarized light reflection derived from a helical structure of the cholesteric liquid crystal. A center wavelength $\lambda$ of this reflection is present at intervals of a pitch length P (=period of helix) of the helical structure of the cholesteric phase, and satisfies a relationship of $\lambda=n\times P$ with respect to the average refractive index n of the cholesteric liquid-crystalline layer. Accordingly, it is possible to adjust the wavelength showing the circularly polarized light reflection by adjusting the pitch length of the helical structure. That is, the n value and the P value may be adjusted to set the center wavelength $\lambda$ in a wavelength range of 380 nm to 780 nm, so as to allow selective transmission (reflection) of light in at least a part of the visible light wavelength range. In addition, the center wavelength $\lambda$ may be set to be 780 nm to 1500 nm and preferably 800 nm to 1500 nm by adjusting the n value and the P value described above, so that any one of right circularly polarized light and left circularly polarized light is selectively transmitted (reflected) in at least a part of the near infrared light wavelength range.

In a case where light is obliquely incident to the cholesteric liquid-crystalline layer, as in a case of using the cholesteric liquid-crystalline layer in the circularly polarized light separation film 1 or the circularly polarized light separation film 2 in the arrangement C of FIG. 1, for example, the center wavelength of the selective reflection is shifted to the short wavelength side. Accordingly, it is preferable to adjust the value of n×P so that $\lambda$ calculated based on the expression of $\lambda=n\times P$ described above becomes a longer wavelength than a wavelength of the selective reflection necessary in accordance with the light source or the light receiving element. When the center wavelength in the selective reflection when a light ray passes through a cholesteric liquid-crystalline layer having a refractive index $n_2$ by an angle of $\theta_2$ with respect to the normal direction of the cholesteric liquid-crystalline layer (screw axis of cholesteric liquid-crystalline layer) is set as $\lambda_d$, a value of $\lambda_d$ is represented with the following expression.

$$\lambda_d=n_2\times P\times\cos\theta_2$$

A value of $\theta_2$ when light is incident to the cholesteric liquid-crystalline layer having a refractive index $n_2$ from the air space having a refractive index of 1.0 by an angle of $\theta_1$ with respect to the normal direction of the cholesteric liquid-crystalline layer is represented with the following expression.

$$\theta_2=\arcsin(\sin\theta_1/n_2)$$

In a case where light is obliquely incident to the cholesteric liquid-crystalline layer, a desired center wavelength may be set by adjusting the n value and the P value based on the expression described above.

Since the pitch length of the cholesteric liquid crystal is dependent on the types of a chiral agent used with the polymerizable liquid crystal compound or added concentration thereof, a desirable pitch length can be obtained by adjusting these. As a measuring method of the sense or pitch of the helix, methods disclosed in "Introduction: Liquid Crystal Experiments" (edited by the Japanese Liquid Crystal Society, Sigma Publications, published in 2007 p. 46) and "Liquid Crystal Handbook" (Liquid Crystal Handbook Editorial Committee, Maruzen Publishing, p. 196) can be used.

In addition, regarding the half-wavelength of the selective reflection (circularly polarized light reflection) range, $\Delta\lambda$ is dependent on a birefringence $\Delta n$ of the liquid crystal compound and the pitch length P and satisfies a relationship of $\Delta\lambda=\Delta n\times P$. Accordingly, the width of the selective reflection range can be controlled by adjusting $\Delta n$. The adjustment of $\Delta n$ can be performed by adjusting the types of polymerizable liquid crystal compound or a mixing ratio thereof, or controlling a temperature at the time of orientation fixation.

Since the width of the circularly polarized light reflection wavelength range in the visible light region is 50 nm to 100 nm with a material in general, it is possible to enlarge the bandwidth of the reflection by laminating several types of cholesteric liquid-crystalline layers having different center wavelengths of the reflected light due to changes in the period P. In addition, in one cholesteric liquid-crystalline layer, it is possible to enlarge the bandwidth of the reflection by gradually changing the period P with respect to a film thickness direction.

In addition, the sense of the reflected circularly polarized light of the cholesteric liquid-crystalline layer coincides with the sense of the helix.

As the circularly polarized light separation layer, a cholesteric liquid-crystalline layer having the sense of helix is right or left may be used, or when lamination is performed in order to increase circularly polarized light, selectivity at a specific wavelength, a plurality of cholesteric liquid-crystalline layers having the same period P and the same sense of helix may be laminated. At that time, a cholesteric liquid-crystalline layer separately prepared by using a method which will be described later may be bonded with an adhesive layer or the like, or a liquid crystal composition including a polymerizable liquid crystal compound may be directly applied to the surface of a preexisting cholesteric liquid-crystalline layer which is formed by a method which will be described later, and laminated by repeating steps of orientation and fixation. By performing the latter method, an orientation alignment of liquid crystal molecules on an air interface side of the cholesteric liquid-crystalline layer previously formed, and an orientation alignment of liquid crystal molecules on the lower side of the cholesteric liquid-crystalline layer formed thereon coincide with each other, and the light polarization properties of the circularly polarized light separation layer are improved.

In addition, a plurality of layers may be laminated in order to enlarge the selective reflection (transmission) wavelength bandwidth, and at that time, the cholesteric liquid-crystalline layer having the same sense of helix may be laminated.

The cholesteric liquid-crystalline layer can selectively allow the transmission of any one of right circularly polarized light and left circularly polarized light even with respect to light incident from any surface, and can separate even light incident from any surface into right circularly polarized light and left circularly polarized light and selectively allow the transmission of any one thereof to the other side surface.

Hereinafter, manufacturing materials and a manufacturing method of the cholesteric liquid-crystalline layer which can be used in the visible light reflection layer or the circularly polarized light separation layer will be described.

As the materials used for the formation of the cholesteric liquid-crystalline layer, a liquid crystal composition containing the polymerizable liquid crystal compound and the chiral agent (optically active compound) are used. If necessary, a liquid crystal composition obtained by additionally mixing in a surfactant or a polymerization initiator and dissolving the mixture in a solution is applied to the base material (a support, an oriented layer, a transparent layer, or the cholesteric liquid-crystalline layer as a lower layer), cholesteric orientation and aging is performed, and fixed to form the cholesteric liquid-crystalline layer.

Polymerizable Liquid Crystal Compound

The polymerizable liquid crystal compound may be a rod-like liquid crystal compound or a disk-like liquid crystal compound, and a rod-like liquid crystal compound is preferably used.

As an example of a rod-like polymerizable liquid crystal compound for forming the cholesteric liquid-crystalline layer, a rod-like nematic liquid crystal compound may be used. As a rod-like nematic liquid crystal compound, azomethines, azoxys, cyano biphenyls, cyanophenyl esters, benzoic acid esters, cyclohexane carboxylic acid phenyl esters, cyanophenyl cyclohexanes, cyano-substituted phenyl pyrimidines, alkoxy—substituted phenyl pyrimidines, phenyl dioxanes, tolanes, and alkenylcyclohexylbenzonitriles are preferably used. Not only a low-molecular-weight liquid crystal compound, but also a high-molecular-weight liquid crystal compound can be used.

A polymerizable cholesteric liquid-crystalline compound is obtained by introducing a polymerizable group to the cholesteric liquid-crystalline compound. Examples of the polymerizable group include an unsaturated coincidence group, an epoxy group, and an aziridinyl group, an unsaturated polymerizable group is preferable and an ethylenically unsaturated polymerizable group is particularly preferable. The polymerizable group can be introduced into molecules of the cholesteric liquid-crystalline compound by various methods. The number of polymerizable groups included by the polymerizable cholesteric liquid-crystalline compound is preferably 1 to 6 and more preferably 1 to 3. Examples of the polymerizable cholesteric liquid-crystalline compound include compounds disclosed in Makromol. Chem., vol. 190, 2255 p, (1989), Advanced Materials, vol. 5, 107 p (1993), U.S. Pat. No. 4,683,327A, U.S. Pat. No. 5,622,648A, U.S. Pat. No. 5,770,107A, WO95/22586A, WO95/24455A, WO97/00600A, WO98/23580A, WO98/52905A, JP1989-272551A (JP-H01-272551A), JP1994-16616A (JP-H06-16616A), JP1995-110469A (JP-H07-110469A), JP1999-80081A (JP-H11-80081), and JP2001-328973A. Two or more types of polymerizable cholesteric liquid-crystalline compound may be used in combination. When two or more types of polymerizable cholesteric liquid-crystalline compound are used in combination, it is possible to decrease the orientation temperature.

In addition, the added amount of the polymerizable liquid crystal compound in the liquid crystal composition is preferably 80 to 99.9% by mass, more preferably 85 to 99.5% by mass, and particularly preferably 90 to 99% by mass, with respect to the solid content mass (mass excluding the solvent) of the liquid crystal composition.

Chiral Agent (Optically Active Compound)

The chiral agent has a function of causing the helical structure of the cholesteric liquid-crystalline phase. Since the sense of helix or the helical pitch varies according to the compound, the chiral compound may be selected according to the purpose.

The chiral agent is not particularly limited, and well-known compounds (for example, Liquid Crystal Device Handbook, third vol. paragraphs 4-3, a chiral agent for TN or STN, p. 199, Japan Society for the Promotion of Science 142th Committee Edition, 1989), isosorbide, or an isomannide derivative can be used.

The chiral agent generally includes asymmetric carbon atoms, but an axial asymmetric compound or a planar asymmetric compound not including asymmetric carbon atoms can be used as the chiral agent. As an example of an axial asymmetric compound or a planar asymmetric compound, binaphthyl, helicene, paracyclophane, and derivatives thereof are included. The chiral agent may include a polymerizable group. When the chiral agent and a curable cholesteric liquid-crystalline compound include a polymerizable group, it is possible to form a polymer including a repeating unit derived from the cholesteric liquid-crystalline compound and a repeating unit derived from the chiral agent, by the polymerization reaction between the polymerizable chiral agent and the polymerizable cholesteric liquid-crystalline compound. In this aspect, the polymerizable group included in the polymerizable chiral agent is preferably the same type of group as the polymerizable group included in the polymerizable cholesteric liquid-crystalline compound. Accordingly, the polymerizable group of the chiral agent is preferably an unsaturated polymerizable group, an epoxy group, or an aziridinyl group, more preferably an unsaturated polymerizable group, and particularly preferably an ethylenically unsaturated polymerizable group.

In addition, the chiral agent may be a liquid crystal compound.

The content of the chiral agent in the liquid crystal composition is preferably 0.01% mol to 200% mol and more preferably 1% mol to 30% mol of the amount of the polymerizable liquid crystal compound.

Polymerization Initiator

The liquid crystal composition preferably contains a polymerization initiator. In a case of causing the polymerization reaction to proceed using the ultraviolet light irradiation, the polymerization initiator used is preferably a photopolymerization initiator which can start the polymerization reaction by an ultraviolet light irradiation. Examples of the photopolymerization initiator include an α-carbonyl compound (disclosed in each specification of U.S. Pat. No. 2,367,661A and U.S. Pat. No. 2,367,670A), acyloin ether (disclosed in the specification of U.S. Pat. No. 2,448,828A), a α-hydrocarbon-substituted aromatic acyloin compound (disclosed in the specification of U.S. Pat. No. 2,722,512A), a polynuclear quinone compound (disclosed in each specification of U.S. Pat. No. 3,046,127A and U.S. Pat. No. 2,951,758), a combination of a triaryl imidazole dimer and p-amino phenyl ketone (disclosed in the specification of U.S. Pat. No. 3,549,367A), acridine and phenazine compounds (disclosed in each specification of JP1985-105667A (JP-S60-105667A) and U.S. Pat. No. 4,239,850A), and an oxadiazole compound (disclosed in the specification of U.S. Pat. No. 4,212,970A).

The content of the photopolymerization initiator in the liquid crystal composition is preferably 0.1% by mass to 20% by mass and more preferably 0.5% by mass to 5% by mass, with respect to the content of the polymerizable liquid crystal compound.

Cross-Linking Agent

The liquid crystal composition may contain an arbitrary cross-linking agent, in order to improve film strength after the curing and durability. As the cross-linking agent, a material which is cured by ultraviolet light, heat, or humidity can be preferably used.

The cross-linking agent is not particularly limited and can be suitably selected according to the purpose, and examples thereof include a multifunctional acrylate compound such as trimethylolpropane tri(meth)acrylate or pentaerythritol tri(meth)acrylate; an epoxy compound such as glycidyl (meth) acrylate or ethylene glycol diglycidyl ether; an aziridine compound such as 2,2-bishydroxymethylbutanol-tris[3-(1-aziridinyl)propionate] or 4,4-bis (ethylene iminocarbonyl amino)diphenylmethane; an isocyanate such as hexamethylene diisocyanate or biuret type isocyanate; a polyoxazoline compound including an oxazoline group as a side chain; and an alkoxysilane compound such as vinyltrimethoxysilane or N-(2-aminoethyl)-3-aminopropyltrimethoxysilane. In addition, a well-known catalyst can be used according to the reactivity of the cross-linking agent and it is possible to improve productivity, in addition to the film strength and durability. These may be used alone or in combination of two or more kinds thereof.

The content of the cross-linking agent is preferably 3% by mass to 20% by mass and more preferably 5% by mass to 15% by mass. When the content of the cross-linking agent is smaller than 3% by mass, an effect of the improvement in crosslinking density may not be obtained, and when the content thereof exceeds 20% by mass, stability of the cholesteric layer may be lower.

Orientation Controlling Agent

An orientation controlling agent which contributes to stable and rapid formation of a planar orientation in a cholesteric liquid-crystalline layer may be added to the liquid crystal composition. Examples of the orientation controlling agent include a fluorine (meth)acrylate polymer disclosed in Paragraphs [0018] to [0043] of JP2007-272185A and compounds represented by Formulae (I) to (IV) disclosed in Paragraphs [0031] to [0034] of JP2012-203237A.

In addition, as the orientation controlling agent, these may be used alone or in combination of two or more kinds thereof.

The added amount of the orientation controlling agent in the liquid crystal composition is preferably 0.01% by mass to 10% by mass, more preferably 0.01% by mass to 5% by mass, and particularly preferably 0.02% by mass to 1% by mass, with respect to the entire mass of the cholesteric liquid-crystalline compound.

Other Additives

Other liquid crystal compositions may contain at least one kind selected from various additives such as a surfactant for adjusting surface tension of a coated film to obtain an even film thickness, and a polymerizable monomer. Further, if necessary, a polymerization inhibitor, an antioxidant, an ultraviolet absorbing agent, a light stabilizer, a coloring material, and metal oxide fine particles can be added to the liquid crystal composition, in a range not decreasing the optical properties.

A cholesteric liquid-crystalline layer in which cholesteric regularity is fixed can be formed, by applying a liquid crystal composition obtained by dissolving the polymerizable liquid crystal compound and the polymerization initiator, and if necessary, the chiral agent and the surfactant in a solvent, on the base material, obtaining a dried coated film, and irradiating this coated film with active light to polymerize the cholesteric liquid-crystalline composition. In addition, a laminated film formed of a plurality of cholesteric layers can be formed by repeating the manufacturing step of the cholesteric layer.

The solvent used in the preparation of the liquid crystal composition is not particularly limited and can be suitably selected according to the purpose, and an organic solvent is preferably used.

The organic solvent is not particularly limited and can be suitably selected according to the purpose, and examples thereof include ketones, alkyl halides, amides, sulfoxides, heterocyclic compounds, hydrocarbons, esters, and ethers. These may be used alone or in combination of two or more kinds thereof. Among these, ketones are particularly preferable, when environmental load is considered.

A method of applying the liquid crystal composition to the base material is not particularly limited and can be suitably selected according to the purpose, and examples thereof include a wire bar coating method, a curtain coating method, an extrusion coating method, a direct gravure coating method, a reverse gravure coating method, a die-coating method, a spin coating method, a dip coating method, a spray coating method, and a slide coating method. In addition, the application can be executed by transferring the liquid crystal composition applied to an additional support to the base material. The liquid crystal molecules are oriented by heating the applied liquid crystal composition. The heating temperature is preferably equal to or lower than 200° C. and more preferably equal to or lower than 130° C. By performing this orientation process, an optical thin film in which the polymerizable liquid crystal compound is twist-oriented so as to have a screw axis substantially orthogonal to a film surface is obtained.

The oriented liquid crystal compound may be farther polymerized. The polymerization may be any of thermal polymerization and photopolymerization performed by light irradiation, and photopolymerization is preferable. The light irradiation is preferably performed using ultraviolet light. The irradiation energy is preferably 20 mJ/cm$^2$ to 50 J/cm$^2$ and more preferably 100 mJ/cm$^2$ to 1500 mJ/cm$^2$. In order to promote the photopolymerization reaction, the light irradiation may be executed under heating conditions or a nitrogen atmosphere. The emitted ultraviolet light wavelength is preferably 350 nm to 430 nm. The polymerization reaction rate is preferably high, preferably equal to or greater than 70%, and more preferably equal to or greater than 80%, from a viewpoint of stability.

The polymerization reaction rate can be determined by measuring the rate of consumption of the polymerizable functional group using an IR absorption spectrum.

In addition, the thickness (total of the plurality of layers, when the plurality of layers are laminated) of the cholesteric liquid-crystalline layer which is the circularly polarized light separation layer is preferably 1 μm to 150 μm, more preferably 1 μm to 100 μm, even more preferably 1.5 μm to 30 μm, and particularly preferably 2 μm to 15 μm.

(Adjustment of Diffuse Reflectance/Specular Reflectance of Cholesteric Liquid-Crystalline Layer)

As a result of the research of the inventors, it is clear that a liquid crystal layer having high diffuse reflectance at a specific wavelength has a small tilt angle of liquid crystal molecules at least on one surface of the layer, preferably both surfaces of the layer and is obtained by setting in-plane orientation azimuth of liquid crystal molecules random. That is, it is possible to adjust the diffuse reflectance at a selective reflection wavelength by adjusting the tilt angle and the in-plane orientation azimuth described above. The liquid crystal orientation azimuth and the tilt angle in the vicinity of the surface of the cholesteric liquid-crystalline layer may be confirmed by observing the vicinity of the film surface of the cross section of the cholesteric liquid-crystalline layer with a transmission electron microscope (TEM) image.

By adjusting the tilt angle and the in-plane orientation azimuth of liquid crystal molecules of the surface of the cholesteric liquid-crystalline layer as described above, it is possible to realize a configuration including an inclination of a screw axis of the cholesteric liquid-crystalline phase on the outermost surface. The expression "including an inclination of a screw axis" means that inclination of the screw axis which will be described later is equal to or greater than 2° in the plane. It is considered that the screw axis of the cholesteric liquid-crystalline phase is distributed with slight undulation in the plane by using the configuration including an inclination of a screw axis of the cholesteric liquid-crystalline phase on the outermost surface. That is, the deviation of the screw axis from the normal direction of the layer can be generated. A scattering layer having high diffuse reflectance/specular reflectance is obtained due to the deviation of the screw axis. A plurality of orientation defects may be generated in this layer.

The inclination of the screw axis on the outermost surface of the cholesteric liquid-crystalline layer can be obtained as follows.

When the cross section of the cholesteric liquid-crystalline layer is observed with TEM, a stripe pattern of bright parts and dark parts can be observed. The stripe pattern is observed so that bright parts and dark parts are repeated in a direction substantially parallel with the layer surface. The repeating of these bright parts and dark parts two times (two bright parts and two dark parts) corresponds to 1 pitch of a helix. The normal direction of the stripe pattern is a screw axis. The inclination of the screw axis on the outermost surface of the cholesteric liquid-crystalline layer can be obtained as an angle formed with a line formed by the first dark part from the outermost surface and the outermost surface on the same side.

By setting the cholesteric liquid-crystalline layer to have a configuration so that the inclination of the screw axis on the outermost surface changes in the plane, it is possible to obtain a reflected light scattering circularly polarized light separation layer having high diffuse reflectance/specular reflectance. The expression "the inclination of the screw axis changes", for example, shows a state in which, when the inclination of the screw axis is measured on an arbitrary straight line of the surface at regular intervals, an increase and a decrease of the inclination are confirmed in a linear progressing direction. The increase and decrease are preferably repeated and it is preferable that the change consecutively occurs.

The outermost surface may be at least any one surfaces (uppermost surface or the lowermost surface) of the cholesteric liquid-crystalline layer or may be both surfaces (uppermost surface or the lowermost surface), and is preferably both surfaces.

A maximum value of the inclination of the screw axis may be approximately equal to or smaller than 20°. The maximum value of the inclination of the screw axis may be 2° C. to 20° and is preferably 5° to 20°.

In this specification, the term "tilt angle" means an angle formed with inclined liquid crystal molecules and a layer plane, and means a maximum angle among angles formed with a direction of a refractive index ellipsoid of a liquid crystal compound having the maximum refractive index and the layer plane. Accordingly, in the rod-like liquid crystal compound having positive optical anisotropy, the tilt angle means an angle formed with a long axis direction of the rod-like liquid crystal compound, that is, a director direction and the layer plane.

The in-plane orientation azimuth of liquid crystal molecules means an azimuth in the plane parallel to the layer in a direction of the liquid crystal molecules having the maximum refractive index. The expression "the in-plane orientation azimuth is random" means a state in which 10% to 20% of the liquid crystal molecules having the in-plane orientation azimuth which is different from the average azimuth of the in-plane orientation azimuths of liquid crystal molecules in the plane by 4° or more can be confirmed by using a TEM.

In this specification, the term "liquid crystal molecules" means molecules of a polymerizable liquid crystal compound in a liquid crystal composition, and means a partial structure corresponding to the polymerizable liquid crystal compound, in a case where the polymerizable liquid crystal compound is polymerized due to a curing reaction of the liquid crystal composition.

A tilt angle of liquid crystal molecules on the surface on the lower layer side when arranging the polymerizable liquid crystal compound when forming the cholesteric liquid-crystalline layer is preferably in a range of 0 degrees to 20 degrees and more preferably 0 degrees to 10 degrees. By controlling the tilt angle to be the values described above, it is possible to set a density of orientation defects and tilt angle distribution of the screw axis to be in preferable ranges.

At the time of the arrangement of the polymerizable liquid crystal compound when forming the cholesteric liquid-crystalline layer for forming the reflected light scattering circularly polarized light separation layer, a tilt angle (pretilt angle) of the liquid crystal molecules on the surface on the lower layer side is set to be small as described above or is preferably horizontal. In addition, in order to decrease orientation uniformity of the liquid crystal molecules, it is preferable not to perform orientation treatment such as rubbing on the surface of a transparent layer, a base material, or other cholesteric liquid-crystalline layer which will be described later to be coated with the liquid crystal composition. It is preferable to use the orientation controlling agent in order to set the tilt angle the liquid crystal molecules on an air interface side of the cholesteric liquid-crystalline layer to be horizontal.

(Laminate Including Linearly Polarized Light Separation Layer and λ/4 Phase Difference Layer)

In the circularly polarized light separation layer formed of the laminate including the linearly polarized light separation layer and the λ/4 phase difference layer, light emitted from the surface of the linearly polarized light separation layer is converted into linearly polarized light by reflection or absorption and then converted into right or left circularly polarized light by passing through the λ/4 phase difference layer. Meanwhile, in a case of light emission from the λ/4 phase difference layer, light in any polarized state becomes linearly polarized light by finally passing through the linearly polarized light separation layer, but specifically, in a case where the incidence ray is circularly polarized light, the light is converted into the linearly polarized light which is parallel to or orthogonal to a transmission axis of the linearly polarized light separation layer by the λ/4 phase difference layer, and accordingly, in order to use the light in recognition of the sense of the incident circularly polarized light, the light is preferably emitted from the λ/4 phase difference layer side, and when using the emitting circularly polarized light, the light is preferably emitted from the linearly polarized light separation layer side.

As the linearly polarized light separation layer, a linear polarizer can be used or a polarizer corresponding to the wavelength range of light used may be used.

Linear Polarizer

As the infrared linear polarizer which can be preferably used, a multilayer dielectric reflection polarizer in which a plurality of layers of resins having refractivity and different refractive indexes from each other are laminated and a thickness and a phase difference value are controlled by stretching, a grid polarizer configured with a number of parallel conductor line arrangements (grid), a polarizer in which metal nanoparticles having shape anisotropy are arranged and fixed, or a polarizer in which dichroic pigments are arranged and fixed, is used. All of these are easily formed in a thin layer shape, a film shape, or a plate shape, and can be formed by simply bonding a sheet-like phase difference layer which will be described later, in a step of forming the circularly polarized light separation layer. Alternatively, the phase difference layer can be formed by directly applying a composition for phase difference layer formation onto the infrared linear polarizer, and thus a thinner circularly polarized light separation layer can be manufactured.

The multilayer dielectric reflection polarizer is a polarizing film which transmits only the light in a vibration direction parallel to the plane transmission axis and reflects the other light. As such a film, a multilayer film disclosed in JP1997-507308A (JP-H09-507308A) can be used. This is obtained by alternatively laminating a layer formed of the transparent dielectric layer 1 not having birefringence in the film surface and a layer formed of the transparent dielectric layer 2 having birefringence in a surface, and is formed so that a refractive index of the transparent dielectric layer 1 coincides with any one of an ordinary light refractive index and an extraordinary light refractive index of the transparent dielectric layer 2. In addition, at least any one of the transparent dielectric layers is configured so that the product (n×d) of the thickness (d) and the refractive index (n) of the transparent dielectric layer becomes ¼ of the wavelength of the light to be reflected. The material for forming the transparent dielectric layers may be materials having light-transmitting properties at the infrared light wavelength used, and examples thereof include polycarbonate, an acrylic resin, polyester, an epoxy resin, polyurethane, polyamide, polyolefin, a cellulose derivative, or silicone (including modified silicone such as silicone polyurea).

The grid polarizer is obtained by providing a plurality of parallel conductor line arrangement structures (grids) having a submicron pitch (pitch shorter than the wavelength of the incidence ray) formed of a good conductor thin film such as aluminum, silver, or gold, on one surface of a polymer film having light-transmitting properties at the infrared light wavelength used, a glass substrate or a silicon (Si) substrate, and a polarizer disclosed in JP2002-328234A can be used. This polarizer functions as a polarizer by reflecting the polarized light component parallel to a grid in the incidence ray and transmitting the polarized light component orthogonal thereto. If necessary, this can be interposed between the glass or an anti-reflection layer can be provided.

The polarizer in which metal nanoparticles having shape anisotropy are arranged and fixed is obtained by orienting and fixing silver halide particles or silver particles having a great aspect ratio. This polarizer is an absorption type linear polarizing plate which absorbs infrared light having an electric field vibration surface in the arrangement direction of the particles and transmits the infrared light in a direction orthogonal thereto. As an example thereof, polarizing plates disclosed in JP1984-83951A (JP-S59-83951A), JP1990-248341A (JP-H02-248341A), and JP2003-139951A can be used.

As the polarizer in which dichroic pigments are arranged and fixed, an infrared polarizing film in which iodine is adsorbed or dichroic dye is doped in PVA (polyvinyl alcohol) and stretched to make polyvinylene can be used. This polarizer absorbs the infrared light having an electric field vibration surface in the stretching direction and transmits the infrared light in the direction orthogonal thereto.

This can obtain the orientation of dichroic pigments by performing dyeing of a PVA layer by passing through the PVA film in a dye composition tank of iodine/iodide and stretching the layer by a factor of 4 to 6 times. The conversion of PVA to polyvinylene can be performed by a hydrochloric acid vapor method disclosed in U.S. Pat. No. 2,445,555A. In addition, in order to improve stability of the materials for polarization, boration of the material into is also performed by using an aqueous borate bath containing boric acid and borax. A commercially available linearly polarized light film manufactured by Edmund Optics Japan can be used as a product corresponding thereto.

The thickness of the linearly polarized light separation layer is preferably 0.05 μm to 300 μm, more preferably 0.2 μm to 150 μm, and even more preferably 0.5 μm to 100 μm.

λ/4 Phase Difference Layer

An inplane slow axis of a phase difference plate is present at an alignment rotated by 45° from the absorption axis or the transmission axis of the polarizing plate. When a single light source such as an LED or a laser is used as the infrared light source, the front surface phase difference of the phase difference plate is desirably a length of ¼ of the center wavelength of the emission wavelength of the light source or "center wavelength*n±¼ of center wavelength (n is an integer)", and for example, when the emission center wavelength of the light source is 1000 nm, the phase difference of 250 nm, 750 nm, 1250 nm, or 1750 nm is preferable. In addition, small dependency of the phase difference on the light incident angle is preferable, and a phase difference plate having a phase difference of a length of ¼ of the center wavelength is most preferable from this viewpoint.

In the sensing system or the sensing method of the invention, when various types of light source having different emission wavelengths are used in combination as the infrared light source, or a light source in which there is a peak in the light emission intensity at greater than or equal to two wavelengths or a light source in which the light emission is performed in a wide wavelength range is used, a case of enlarging the wavelength range showing the circularly polarized light selectivity is considered. Even in such a case, the phase difference plate described above can be used, but it is more preferably to use a phase difference plate having a wide range. A phase difference plate having a wide range is a phase difference plate in which a phase difference angle is constant over the wide wavelength range, and examples thereof include a laminated phase difference plate in which phase difference layers having different wavelength dispersions of the birefringence from each other are set to be orthogonal to the slow axis thereof to have a wide range, a polymer film in which substituents having different wavelength dispersions of the birefringence from each other are set to be orthogonal to an arrangement axis thereof using the principle described above at a molecular level to perform the orientation formation, or a phase difference plate in which a layer of λ/2 which is the phase difference with respect to the wavelength (λ) in the wavelength range used and a layer of λ/4 are laminated by being caused to intersect the slow axis thereof at 60 degrees.

Examples of the material of the phase difference plate include crystalline glass or crystal of an inorganic material, a polymer such as polycarbonate, an acrylic resin, polyester, an epoxy resin, polyurethane, polyamide, polyolefin, a cellulose derivative, or silicone (including modified silicone such as silicone polyurea), or a material in which polymerizable liquid crystal compounds or polymer liquid crystal compounds are arranged and fixed.

The thickness of the λ/4 layer is preferably 0.2 μm to 300 μm, more preferably 0.5 μm to 150 μm, and even more preferably 1 μm to 80 μm.

<Other Layers>

The circularly polarized light separation film may include other layers such as a support, an orientation layer for causing the orientation of the liquid crystal compound, an adhesion layer for adhering the circularly polarized light separation layer and the visible light shielding layer to each other, and a light shielding layer for not allowing the transmission of light at a wavelength beyond the specific wavelength range used in the sensing.

(Support)

The support is not particularly limited and a plastic film or glass may be used as an example. It is preferable that the support does not have a property of offsetting the optical properties of the visible light shielding layer or the circularly polarized light separation layer, and the support is generally transparent and preferably has low birefringence. Examples of the plastic film include polyester such as polyethylene terephthalate (PET), polycarbonate, an acrylic resin, an epoxy resin, polyurethane, polyamide, polyolefin, a cellulose derivative, and silicone. The support used for manufacturing the cholesteric liquid-crystalline layer may be peeled off from the circularly polarized light separation film.

In a case of using a circularly polarized light separation film including a support and a circularly polarized light separation layer in the emission unit, it is preferable that the support side of the circularly polarized light separation layer becomes the light source side. In addition, in a case of using a circularly polarized light separation film including a support and a circularly polarized light separation layer in the detection unit, the support side of the circularly polarized light separation layer becomes the light receiving element side.

(Orientation Layer)

The orientation film can be provided by means of rubbing treatment of an organic compound and a polymer (a resin such as polyimide, polyvinyl alcohol, polyester, polyarylate, polyamideimde, polyetherimide, polyamide, or modified polyamide), oblique evaporation of an inorganic material, formation of a layer having a microgroove, or accumulation of an organic compound (for example, ω-tricosanoic acid, dioctadecyl methyl ammonium chloride, or methyl stearate) by a Langmuir-Blodgett method (LB film). In addition, an orientation layer which has an orientation function by applying an electric field, applying a magnetic field, or performing light irradiation is also known. Among these, the orientation film formed by the rubbing treatment of the polymer is particularly preferable. The rubbing treatment can be executed by rubbing the surface of the polymer layer in a given direction with paper or a fabric.

The liquid crystal composition may be applied to the surface of the support or the surface on which the rubbing treatment of the support is performed, without providing the orientation layer.

(Transparent Layer)

At the time of preparing the reflected light scattering circularly polarized light separation layer, a transparent layer may be included as a lower layer coated with a liquid crystal composition when forming the cholesteric liquid-crystalline layer. As the transparent layer, a layer formed of a material which applies a low pretilt angle to the polymerizable liquid crystal compound molecules in the liquid crystal composition provided on the surface thereof can be preferably used.

As the transparent layer, a layer obtained by applying and curing a non-liquid crystal polymerizable composition including (meth)acrylate monomers, gelatin, or urethane monomers can be used. An acrylic layer obtained by applying and curing a layer including (meth)acrylate monomers is isotropic in the plane, for example, and accordingly, when a liquid crystal layer is formed without performing rubbing treatment on the surface of the acrylic layer, the inplane orientation azimuth of liquid crystals coming into contact with the acrylic layer becomes random.

Thus, the cholesteric liquid-crystalline layer formed by applying the liquid crystal composition to the surface of the acrylic layer can be set as a layer having orientation defects.

When a liquid crystal layer is formed on the liquid crystal layer having orientation defects, a liquid crystal layer having orientation defects can be formed in the same manner.

In addition, as the transparent layer, a resin such as polyimide (SUNEVER 130 which is polyimide varnish manufactured by Nissan Chemical Industries, Ltd.), polyvinyl alcohol, polyester, polyarylate, polyamideimide, polyetherimide, polyamide, or modified polyamide may be used. It is preferable not to perform rubbing treatment (for example, rubbing treatment of rubbing a surface of a polymer layer in a certain direction by using paper or cloth) on the surface of the transparent layer coated with the liquid crystal composition, in order to form a cholesteric liquid-crystalline layer having high diffuse reflectance.

A thickness of the transparent layer is preferably 0.01 to 50 μm and more preferably 0.05 to 20 μm.

(Adhesive Layer)

An adhesive may be a hot melt type, a heat curing type, a photocuring type, a reactive curing type, and a pressure sensitive adhesion type which does not need curing from a viewpoint of the curing method, and as a material of each type, acrylate, urethane, urethane acrylate, epoxy, epoxy acrylate, polyolefin, modified olefin, polypropylene, ethylene vinyl alcohol, vinyl chloride, chloroprene rubber, cyanoacrylate, polyamide, polyimide, polystyrene, and polyvinyl butyral compounds can be used. The curing method is preferably the photocuring type, from the viewpoints of workability and productivity, and as the material, an acrylate, urethane acrylate, or epoxy acrylate compound is preferably used, from the viewpoints of optical transparency and heat resistance.

(Light Shielding Layer)

The circularly polarized light separation film preferably has low light transmittance with respect to light at a wavelength beyond the specific wavelength range. The light shielding layer is provided in order to shield light at a wavelength beyond the specific wavelength range.

As the light shielding layer, a light reflection layer or a light absorption layer is used.

As an example of the light reflection layer, a dielectric multilayer film and a cholesteric liquid-crystalline layer can be used.

The dielectric multilayer film which is a transparent dielectric is obtained by laminating a plurality of layers of inorganic oxide or an organic polymer material having different refractive indexes. A layer of the inorganic oxide can be, for example, formed on a surface of glass or a heat resistant polymer film by a sputtering method. Meanwhile, as an example of the inorganic polymer material, polycarbonate, an acrylic resin, polyester, an epoxy resin, polyurethane, polyamide, polyolefin, or silicone (including modified silicone such as silicone polyurea) is used, and the inorganic polymer material can be manufactured based on a method disclosed in JP1997-507308A (JP-H09-507308A).

The reflectance of the cholesteric liquid-crystalline layer at a reflection wavelength increases as the cholesteric liquid-crystalline layer becomes thicker, but in a general liquid crystal material, saturation is obtained with a thickness of 2 to 8 μm in the wavelength range of visible light, and the reflection occurs with respect to only the circularly polarized light on one side, and accordingly, the reflectance is 50% at most. in order to perform the light reflection regardless of the sense of the circularly polarized light and to set the reflectance of natural light to be equal to or greater than 50%, as the visible light reflection layer, a laminate in which a cholesteric liquid-crystalline layer having right sense of helix and a cholesteric liquid-crystalline layer having left sense of helix having the same period P, or a laminate formed of cholesteric liquid-crystalline layers having the same period P and the same sense of helix, and a phase difference film having a phase difference of a half wavelength with respect to the center wavelength of the circularly polarized light reflection of the cholesteric liquid-crystalline layer disposed therebetween can be used.

As the light absorption layer, a layer formed by applying a dispersion obtained by dispersing a colorant such as a pigment or a dye in a solvent containing a dispersing agent and a binder or a monomer on a base material (preferably a material having a sufficient light-transmitting property in the infrared light wavelength range detected by the light receiving element), a layer obtained by directly dying a surface of a polymer base material using a dye, or a layer formed of a polymer material containing a dye can be used.

EXAMPLES

Hereinafter, the invention will be described in more detail with reference to Examples. The materials, the reagents, the amounts of materials, the proportions thereof, the operations, and the like can be suitably modified within a range not departing from a gist of the invention. Accordingly, the range of the invention is not limited to the following Examples.

<Preparation of Reflection Film MR-1 (Mirror Type)>

The rubbing treatment was performed on a PET surface of COSMOSHINE A-4100 manufactured by Toyobo Co., Ltd. (thickness of 75 μm) which is not subjected easy adhesion treatment, and a coating solution 1 shown in Table 1 was applied at room temperature so that a thickness of a dried film after drying becomes 5 μm. After drying the coating layer at room temperature for 30 seconds, the coating layer was heated in the atmosphere at 85° C. for 2 minutes, and irradiated with UV lights for 6 to 12 seconds at the output of 60% by using a D bulb (lamp, 90 mW/cm) manufactured by Fusion UV Inc. at 30° C. to prepare a liquid crystal layer and obtain a reflection film MR-1.

<Preparation of Reflection Film MR-2 to MR-5 (Mirror Type)>

Reflection films MR-2 to MR-5 were prepared in the same procedure as in the preparation of the reflection film MR-1, except for respectively using coating solutions 2 to 5 shown in Table 1, instead of the coating solution 1.

<Preparation of Reflection Film SC-1 (Scattering Type)>

A solution B shown in Table 2 was applied to one surface of COSMOSHINE A-4300 manufactured by Toyobo Co., Ltd. (thickness of 75 μm) at room temperature by using a wire bar so that a thickness of a dried film after drying becomes 8 μm. After drying the coating layer at room temperature for 30 seconds, the coating layer was heated in the atmosphere at 85° C. for 2 minutes, and irradiated with UV lights for 6 to 12 seconds at the output of 60% by using a D bulb (lamp, 90 mW/cm) manufactured by Fusion UV Inc. at 30° C. to obtain an acrylic layer. The coating solution 1 shown in Table 1 was applied onto the acrylic layer obtained as described above at room temperature so that a thickness of the dried film after drying becomes 5 μm, without performing the rubbing treatment. The obtained coating film was dried, heated, and irradiated with UV light in the same manner as described above to prepare a liquid crystal layer and obtain a reflection film SC-1.

<Preparation of Reflection Film. SC-2 to SC-5 (Scattering Type)>

Reflection films SC-2 to SC-5 were prepared in the same procedure as in the preparation of the reflection film SC-1, except for respectively using coating solutions 2 to 5 shown in Table 1, instead of the coating solution 1.

As shown in Table 1, the reflection films having the same coating solution for forming a circularly polarized light separation layer respectively had the same selective reflection center wavelength and sense of helix.

TABLE 1

|  |  | Coating solution 1 (part by mass) | Coating solution 2 (part by mass) | Coating solution 3 (part by mass) | Coating solution 4 (part by mass) | Coating solution 5 (part by mass) |
| --- | --- | --- | --- | --- | --- | --- |
| Liquid crystal compound | Compound 1 | 80 | 80 | 80 | 80 | 80 |
| Liquid crystal compound | Compound 2 | 20 | 20 | 20 | 20 | 20 |
| Polymerization initiator | Irg-819 Manufactured by BASF | 4 | 4 | 4 | 4 | 4 |
| Orientation controlling agent | Compound 3 | 0.07 | 0.07 | 0.07 | 0.07 | 0.07 |
| Orientation controlling agent | Compound 4 | 0.03 | 0.03 | 0.03 | 0.03 | 0.03 |

TABLE 1-continued

| | | Coating solution 1 (part by mass) | Coating solution 2 (part by mass) | Coating solution 3 (part by mass) | Coating solution 4 (part by mass) | Coating solution 5 (part by mass) |
|---|---|---|---|---|---|---|
| Chiral agent | Paliocolor LC-756 Manufactured by BASF | 6.73 | 3.44 | 0 | 6.27 | 2.91 |
| Chiral agent | Compound 5 | 0 | 0 | 5.60 | 0 | 0 |
| Solvent | Methyl ethyl ketone (MEK) | Amount of solvent was adjusted so that concentration of solid contents becomes 35% by mass. | | | | |
| | | ↓ | ↓ | ↓ | ↓ | ↓ |
| | Film (mirror type) | MR-1 | MR-2 | MR-3 | MR-4 | MR-5 |
| | Film (scattering type) | SC-1 | SC-2 | SC-3 | SC-4 | SC-5 |
| | Reflection center wavelength | 450 nm | 880 nm | 880 nm | 483 nm | 1040 nm |
| | Sense of helix | Right | Right | Left | Right | Right |

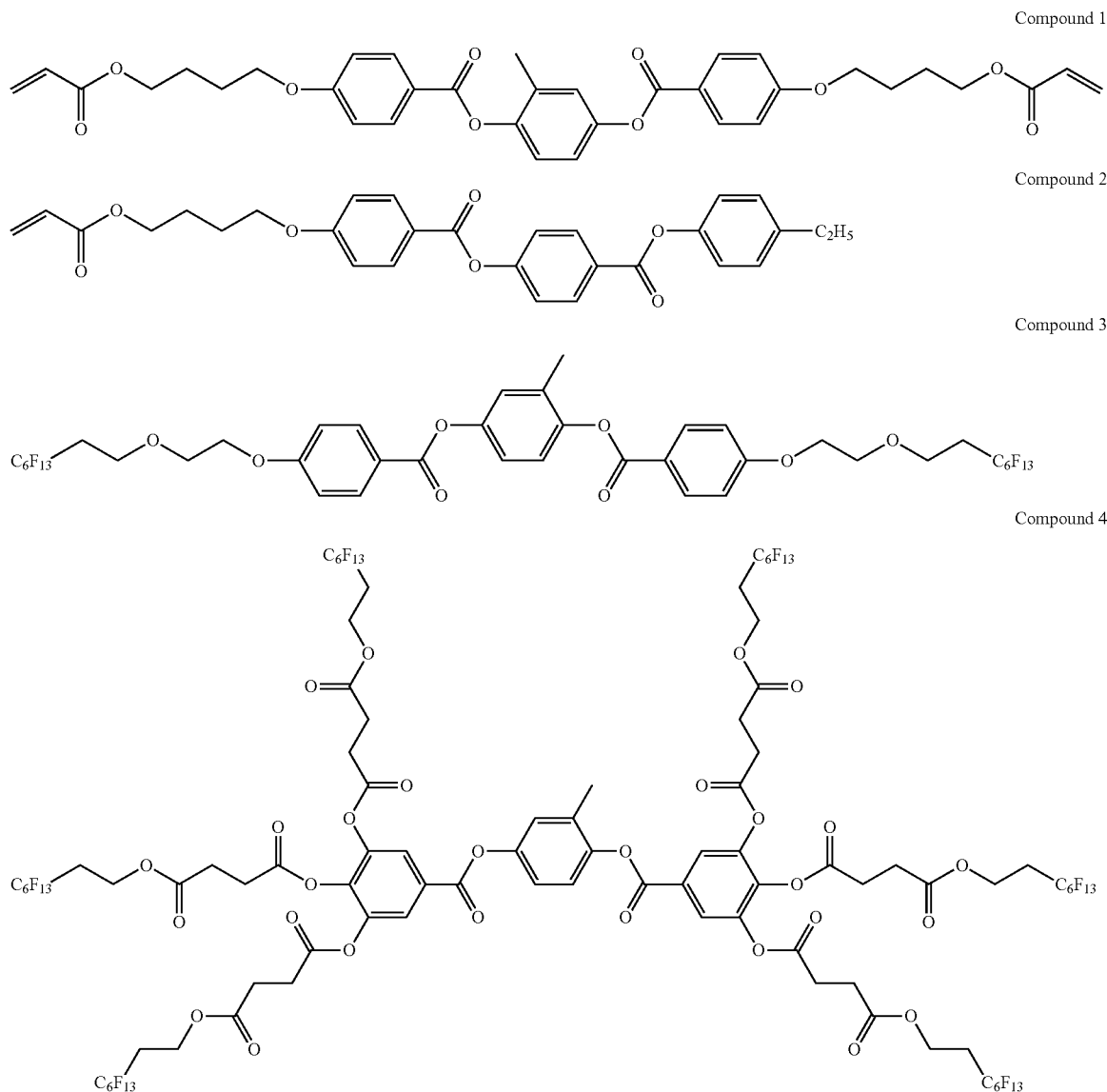

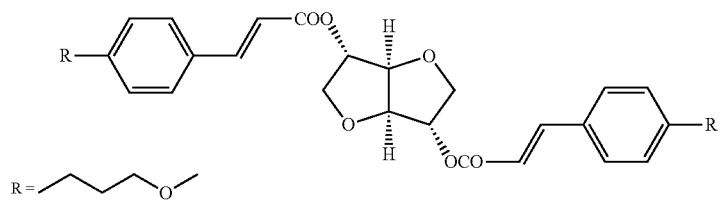

Compound 5

TABLE 2

| Material (type) | Name of material (company) | Coating solution (B) |
|---|---|---|
| Acrylic monomer | Viscoat 360 (manufactured by Osaka Organic Chemical Industry Ltd.) | 100 parts by mass |
| Polymerization initiator | Irg-819(BASF) | 4 parts by mass |
| Surfactant | Compound 2 | 0.03 parts by mass |
| Solvent | 2-butanone (Wako Pure Chemical Industries, Ltd.) | Suitably adjusted in accordance with film thickness |

<Preparation of Circularly Polarized Light Separation Films a1 to a8>

Two kinds of the prepared reflection films MR-1 to MR-5 and the reflection films SC-1 to SC-5 were bonded to each other or the films are used alone, as shown in the following Table 3, to prepare circularly polarized light separation films a1 to a8. When bonding the MR film and the SC film prepared as described above to each other, the bonding is performed with the following procedure.

A UV curable adhesive Exp. U12034-6 manufactured by DIC Corporation was applied to a surface of a reflection film of a lower layer shown in Table 3 on a liquid crystal layer side by using a wire bar at room temperature so that a thickness of a dried film after drying becomes 5 μm. This coated surface and a surface of a reflection film of an upper layer shown in Table 3 on the liquid crystal layer side were bonded to each other so that air bubbles were not generated, and were UV-irradiated using a D bulb (lamp 90 mW/cm) manufactured by Fusion UV Inc., for 12 seconds with output of 60% at 30° C. Then, the PET film which was the support of the upper layer was peeled off.

In Table 3, PUREACE W-142 manufactured by Teijin Limited. was used as a λ/4 plate and HLC 2-5618RE manufactured by Sanritsu Corporation was used as a linear polarizer. The adhesion between the λ/4 plate and the linear polarizer was performed by using a UV curable adhesive Exp. U12034-6 manufactured by DIC Corporation in the same manner as in the bonding of the MR film and the SC film described above.

Examples 1 to 9 and Comparative Example 1

Figure 2B:
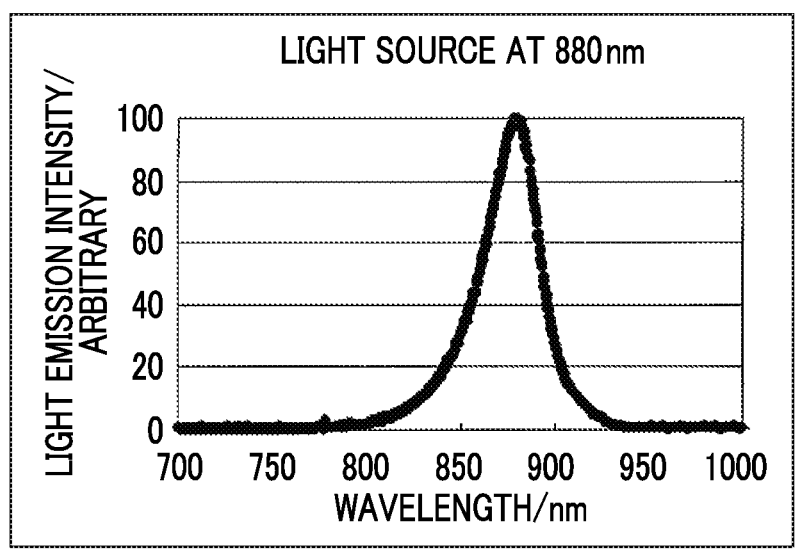

The prepared circularly polarized light separation films a1 to a8 were combined with the emission unit and the detection unit as shown in Table 4, and the sample sensing was performed. In Examples 1 to 9, the senses of helix of the circularly polarized light separation films used in the emission unit and the detection unit are the same as each other, and in Comparative Example 1, the senses of the helix are opposite to each other. As the light source, an LED having the center wavelength of light emission intensity at light emitting spectra of 450 nm or 880 nm shown in FIG. 2 was used, as the light receiving element (light detector), a light power meter ML9001A manufactured by Anritsu Corporation was used, and as a sample, 5-dollar banknotes of Canada (including a transparent part and an opaque part) was used. The light source, the light detector, and the circularly polarized light separation film was disposed as shown in the arrangements A to C of FIG. 1 as shown in Table 3. The sample was disposed so as to have a short side direction of the sample plane in the plane of the drawing of the target object movement unit shown in FIG. 1 and a long side direction of the sample plane in a depth direction of the drawing, and the sample was set to be present on the intersection between the light path and the target object movement unit at the time of the sensing.

When installing the circularly polarized light separation films a1 to a8 in the light source, the lower layer side shown in Table 3 is set to become the light source side, and when installing the circularly polarized light separation films in the light detector, the lower layer side shown in Table 3 is set to become the light detector side. The tilt angle and the wavelength of the light source were selected as shown in Table 4.

The output of the light detector in a case where the sample is installed with a transparent part and a non-transparent part and a case where no sample is present is shown in Table 4. Table 4 shows a value when the output of the detector in a state where the circularly polarized light separation film is installed in neither of the light source and the detector is 100. The S/N shown in Table 4 is a ratio of a measurement value without the sample to a measurement value of the transpar-

TABLE 3

| | Circularly polarized light separation film a1 | Circularly polarized light separation film a2 | Circularly polarized light separation film a3 | Circularly polarized light separation film a4 | Circularly polarized light separation film a5 | Circularly polarized light separation film a6 | Circularly polarized light separation film a7 | Circularly polarized light separation film a8 |
|---|---|---|---|---|---|---|---|---|
| Upper layer | MR-1 | SC-1 | MR-2 | SC-2 | SC-3 | SC-4 | SC-5 | λ/4 plate |
| Lower layer | None | MR-1 | None | MR-2 | MR-3 | MR-4 | MR-5 | linear polarizer | ent part. When this ratio great, it is considered that the erroneous sensing hardly occurs.

TABLE 4

| | Light source light emitting wavelength | Light source side Circularly polarized light separation film | Light receiving side Circularly polarized light separation film | Film arrangement | Sample tilt angle | Output of detector | | | S/N |
| | | | | | | No sample | Transparent part | Shielding unit | |
|---|---|---|---|---|---|---|---|---|---|
| Example 1 | 450 nm | a1 | a1 | B | 35 degrees | 46 | 6 | 0.2 | 7.7 |
| Example 2 | 450 nm | a2 | a2 | B | 35 degrees | 44 | 3 | 0.1 | 14.7 |
| Example 3 | 880 nm | a3 | a3 | B | 57 degrees | 46 | 7 | 0.3 | 6.6 |
| Example 4 | 880 nm | a4 | a4 | B | 57 degrees | 44 | 3 | 0.3 | 14.7 |
| Example 5 | 880 nm | a5 | a5 | B | 57 degrees | 44 | 4 | 0.3 | 11.0 |
| Example 6 | 450 nm | a6 | a6 | C | 35 degrees | 41 | 5 | 0.2 | 8.2 |
| Example 7 | 880 nm | a7 | a7 | C | 57 degrees | 37 | 6 | 0.3 | 6.2 |
| Example 8 | 450 nm | a8 | a8 | B | 35 degrees | 34 | 4 | 0.1 | 8.5 |
| Example 9 | 880 nm | a4 | a4 | A | 0 degree | 44 | 38 | 0.3 | 1.2 |
| Comparative Example 1 | 880 nm | a4 | a5 | A | 0 degree | 0.5 | 0.8 | 0.3 | 0.63 |

EXPLANATION OF REFERENCES

1: circularly polarized light separation film 1
2: circularly polarized light separation film 2
11: circularly polarized light separation film 11
12: circularly polarized light separation film 12
16: mirror reflection member
22: light source
23: light receiving element
24: target object movement unit
25: light source
32: emission unit
33: detection unit

What is claimed is:
1. A system which senses a target object, which is system I or system II as follows:
system I comprising:
an emission unit which emits circularly polarized light;
a target object movement unit; and
a detection unit which senses circularly polarized light, in this order,
wherein the detection unit is at a position where light emitted from the emission unit is incident,
a light path of light where the light emitted from the emission unit is incident to the detection unit intersects with the target object movement unit, and
the sense of circularly polarized light selectively emitted by the emission unit and the sense of circularly polarized light selectively sensed by the detection unit are the same as each other,
the emission unit includes a light source and a first circularly polarized light separation film,
the detection unit includes a second circularly polarized light separation film and a light receiving element,
the light source, the first circularly polarized light separation film, the target object movement unit, the second circularly polarized light separation film, and the light receiving element are disposed in this order, and
the first circularly polarized light separation film and the second circularly polarized light separation film comprise a reflected light scattering circularly polarized light separation layer and a reflected light non-scattering circularly polarized light separation layer, respec- tively, and allow selective transmission of circularly polarized light having the same sense; or
system II comprising:
an emission unit which emits circularly polarized light;
a detection unit which senses circularly polarized light;
a target object movement unit; and
a mirror reflection member,
wherein the target object movement unit is between the emission unit and the mirror reflection member, between the mirror reflection member and the detection unit, or any combination thereof,
the emission unit and the detection unit are at a position where the light emitted from the emission unit is mirror-reflected by the mirror reflection member and incident to the detection unit,
a light path of the light which is emitted from the emission unit and incident to the mirror reflection member, a light path of the light which is sensed by the detection unit due to the reflection of the incident light by the mirror reflection member, or any combination thereof intersects with the target object movement unit, and
the sense of circularly polarized light selectively emitted by the emission unit and the sense of circularly polarized light selectively sensed by the detection unit are opposite from each other,
the emission unit includes a light source and a first circularly polarized light separation film,
the detection unit includes a second circularly polarized light separation film and a light receiving element,
the light source, the first circularly polarized light separation film, and the mirror reflection member are included in this order,
the mirror reflection member, the second circularly polarized light separation film, and the light receiving element are included in this order, and
the first circularly polarized light separation film and the second circularly polarized light separation film comprise a reflected light scattering circularly polarized light separation layer and a reflected light non-scattering circularly polarized light separation layer, respectively, and allow selective transmission of circularly polarized light having opposite senses.
2. The system according to claim 1,
wherein the first circularly polarized light separation film, the second circularly polarized light separation film included in system I, and the first circularly polarized light separation film and the second circularly polarized light separation film included in system II are all films including circularly polarized light separation layers obtained by fixing a cholesteric liquid-crystalline phase.

3. The system according to claim 1, which is system I.

4. The system according to claim 1, which is system II.

5. The system according to claim 1,
wherein the target object is an object including a transparent part.

6. The system according to claim 1,
wherein the target object is an object including a transparent part and an opaque part.

7. The system according to claim 1,
wherein the target object has a sheet shape.

8. The system according to claim 7,
wherein the target object is a banknote.

9. The system according to claim 7,
wherein the target object is a banknote including a transparent part.

10. The system according to claim 7,
wherein the target object movement unit is disposed so that the light path is tilted with respect to a normal direction of the plane of the target object, when the target object passes through the light path.

11. The system according to claim 10,
wherein tilt angle of the tilt is greater than 20° and equal to or smaller than 70°.

12. The system according to claim 10,
wherein the target object is a banknote and the tilt direction is parallel with a short side direction of the banknote.

13. The system according to claim 11,
wherein the target object is a banknote and the tilt direction is parallel with a short side direction of the banknote.

14. A method of sensing a target object comprising:
emitting circularly polarized light from a light source through a first circularly polarized light separation film including a reflected light scattering circularly polarized light separation layer and a reflected light non-scattering circularly polarized light separation layer;
sensing the emitted circularly polarized light through a second circularly polarized light separation film including the reflected light scattering circularly polarized light separation layer and the reflected light non-scattering circularly polarized light separation layer;
detecting a target object due to a change in light intensity of the circularly polarized light sensed when the target object passes to cross a light path of the circularly polarized light, in a state where circularly polarized light selectively including any one sense of right circularly polarized light and left circularly polarized light is sensed,
wherein the sense of the circularly polarized light selectively emitted and the sense of circularly polarized light selectively sensed are the same as each other;
wherein the target object is a banknote including a transparent part.

15. The method according to claim 14,
wherein the change is a decrease.

16. The method according to claim 14,
wherein the target object is an object including a transparent part and an opaque part.

17. The method according to claim 14,
wherein the target object passes through the light path so that the light path is tilted with respect to a normal direction of the plane of the target object.

18. The system according to claim 17,
wherein tilt angle of the tilt is greater than 20° and equal to or smaller than 70°.

19. The method according to claim 17,
wherein the target object is a banknote and the tilt direction is parallel with a short side direction of the banknote.

20. The method according to claim 18,
wherein the target object is a banknote and the tilt direction is parallel with a short side direction of the banknote.

21. The system according to claim 17,
wherein tilt angle of the tilt is greater than 30° and equal to or smaller than 60°.

22. A system which senses a target object,
which is system I or system II as follows:
system I comprising:
an emission unit which emits circularly polarized light;
a target object movement unit; and
a detection unit which senses circularly polarized light, in this order,
wherein the detection unit is at a position where light emitted from the emission unit is incident,
a light path of light where the light emitted from the emission unit is incident to the detection unit intersects with the target object movement unit, and
the sense of circularly polarized light selectively emitted by the emission unit and the sense of circularly polarized light selectively sensed by the detection unit are the same as each other,
the emission unit includes a light source and a first circularly polarized light separation film,
the detection unit includes a second circularly polarized light separation film and a light receiving element,
the light source, the first circularly polarized light separation film, the target object movement unit, the second circularly polarized light separation film, and the light receiving element are disposed in this order, and
the first circularly polarized light separation film and the second circularly polarized light separation film comprise a reflected light scattering circularly polarized light separation layer and a reflected light non-scattering circularly polarized light separation layer, respectively, and allow selective transmission of circularly polarized light having the same sense; or
system II comprising:
an emission unit which emits circularly polarized light;
a detection unit which senses circularly polarized light;
a target object movement unit; and
a mirror reflection member,
wherein the target object movement unit is between the emission unit and the mirror reflection member, between the mirror reflection member and the detection unit, or any combination thereof,
the emission unit and the detection unit are at a position where the light emitted from the emission unit is mirror-reflected by the mirror reflection member and incident to the detection unit,
a light path of the light which is emitted from the emission unit and incident to the mirror reflection member, a light path of the light which is sensed by the detection unit due to the reflection of the incident light by the mirror reflection member, or any combination thereof intersects with the target object movement unit, and the sense of circularly polarized light selectively emitted by the emission unit and the sense of circularly polarized light selectively sensed by the detection unit are opposite from each other, the emission unit includes a light source and a first circularly polarized light separation film, the detection unit includes a second circularly polarized light separation film and a light receiving element, the light source, the first circularly polarized light separation film, and the mirror reflection member are included in this order, the mirror reflection member, the second circularly polarized light separation film, and the light receiving element are included in this order, and the first circularly polarized light separation film and the second circularly polarized light separation film comprise a reflected light scattering circularly polarized light separation layer and a reflected light non-scattering circularly polarized light separation layer, respectively, and allow selective transmission of circularly polarized light having opposite senses, wherein the target object has a sheet shape, wherein the target object movement unit is disposed so that the light path is tilted with respect to a normal direction of the plane of the target object, when the target object passes through the light path, wherein tilt angle of the tilt is greater than 30° and equal to or smaller than 60°.

\* \* \* \* \*